(12) United States Patent
Kinoshita et al.

(10) Patent No.: US 8,088,580 B2
(45) Date of Patent: *Jan. 3, 2012

(54) RNA DETECTION METHOD

(75) Inventors: Kenji Kinoshita, Hyogo (JP); Kanehisa Yokoyama, Tokyo (JP); Kentaro Fujimoto, Tokyo (JP); Toru Yakabe, Tokyo (JP); Shin Saito, Tokyo (JP); Kazuhiko Fujiwara, Tokyo (JP)

(73) Assignee: Sumitomo Bakelite Company, Ltd., Tokyo (JP)

( * ) Notice: Subject to any disclaimer, the term of this patent is extended or adjusted under 35 U.S.C. 154(b) by 366 days.

This patent is subject to a terminal disclaimer.

(21) Appl. No.: 12/227,904

(22) PCT Filed: Jun. 1, 2007

(86) PCT No.: PCT/JP2007/000592
§ 371 (c)(1),
(2), (4) Date: Dec. 2, 2008

(87) PCT Pub. No.: WO2007/141912
PCT Pub. Date: Dec. 13, 2007

(65) Prior Publication Data
US 2009/0137406 A1     May 28, 2009

(30) Foreign Application Priority Data

Jun. 7, 2006 (JP) .................................. 2006-159097
Sep. 25, 2006 (JP) .................................. 2006-258266

(51) Int. Cl.
*C12Q 1/68* (2006.01)
*C12P 19/34* (2006.01)
*C07H 21/02* (2006.01)
*C07H 21/04* (2006.01)

(52) U.S. Cl. ............... 435/6.11; 435/6.12; 435/91.1; 536/23.1

(58) Field of Classification Search ........... 435/6, 287.1, 435/287.2, 91.1; 536/23.1
See application file for complete search history.

(56) References Cited

U.S. PATENT DOCUMENTS

| 6,844,158 B1 | 1/2005 | Mitsuhashi |
| 2002/0095073 A1* | 7/2002 | Jacobs et al. ................ 600/300 |
| 2003/0138809 A1* | 7/2003 | Williams et al. ............... 435/6 |

(Continued)

FOREIGN PATENT DOCUMENTS

JP     2002-505080     2/2002

(Continued)

OTHER PUBLICATIONS

International Search Report.

(Continued)

*Primary Examiner* — Robert T. Crow
(74) *Attorney, Agent, or Firm* — Smith, Gambrell & Russell, LLP

(57) ABSTRACT

The present invention provides an RNA detection method detecting, from a reaction system containing a target sample, a target RNA chain originated from the target sample, using a surface having on the surface thereof a polymer substance which contains a first unit having a group derived from a phosphate ester composing the hydrophilic portion of a phospholipid and a second unit having a carboxylic acid derivative group composed of an electron-attractive substitutional group bound to a carbonyl group, while being provided with at least one reaction space, the reaction space having an immobilized nucleic acid primer immobilized therein.

34 Claims, 25 Drawing Sheets

U.S. PATENT DOCUMENTS

| | | | |
|---|---|---|---|
| 2003/0152998 A1 | 8/2003 | Mitsuhashi | |
| 2003/0157550 A1 | 8/2003 | Mitsuhashi | |
| 2004/0058365 A1* | 3/2004 | Panzer et al. | 435/6 |
| 2005/0009051 A1* | 1/2005 | Han et al. | 435/6 |
| 2005/0130167 A1* | 6/2005 | Bao et al. | 435/6 |
| 2005/0208093 A1* | 9/2005 | Glauser et al. | 424/423 |
| 2006/0014182 A1* | 1/2006 | Kurn | 435/6 |
| 2007/0238679 A1* | 10/2007 | Rank et al. | 514/44 |

FOREIGN PATENT DOCUMENTS

| | | |
|---|---|---|
| JP | 2003-523183 | 8/2003 |
| JP | 2007-074928 | 3/2007 |
| WO | 01-48242 | 7/2001 |
| WO | 2005/029095 | 3/2005 |

OTHER PUBLICATIONS

Takashi Ishikawa, et al., "Construction of cDNA bank from biopsy specimens for multiple gene analysis of cancer", Clinical Chemistry, 1997, vol. 42, No. 5, pp. 764-770.

* cited by examiner

Fig.1-a
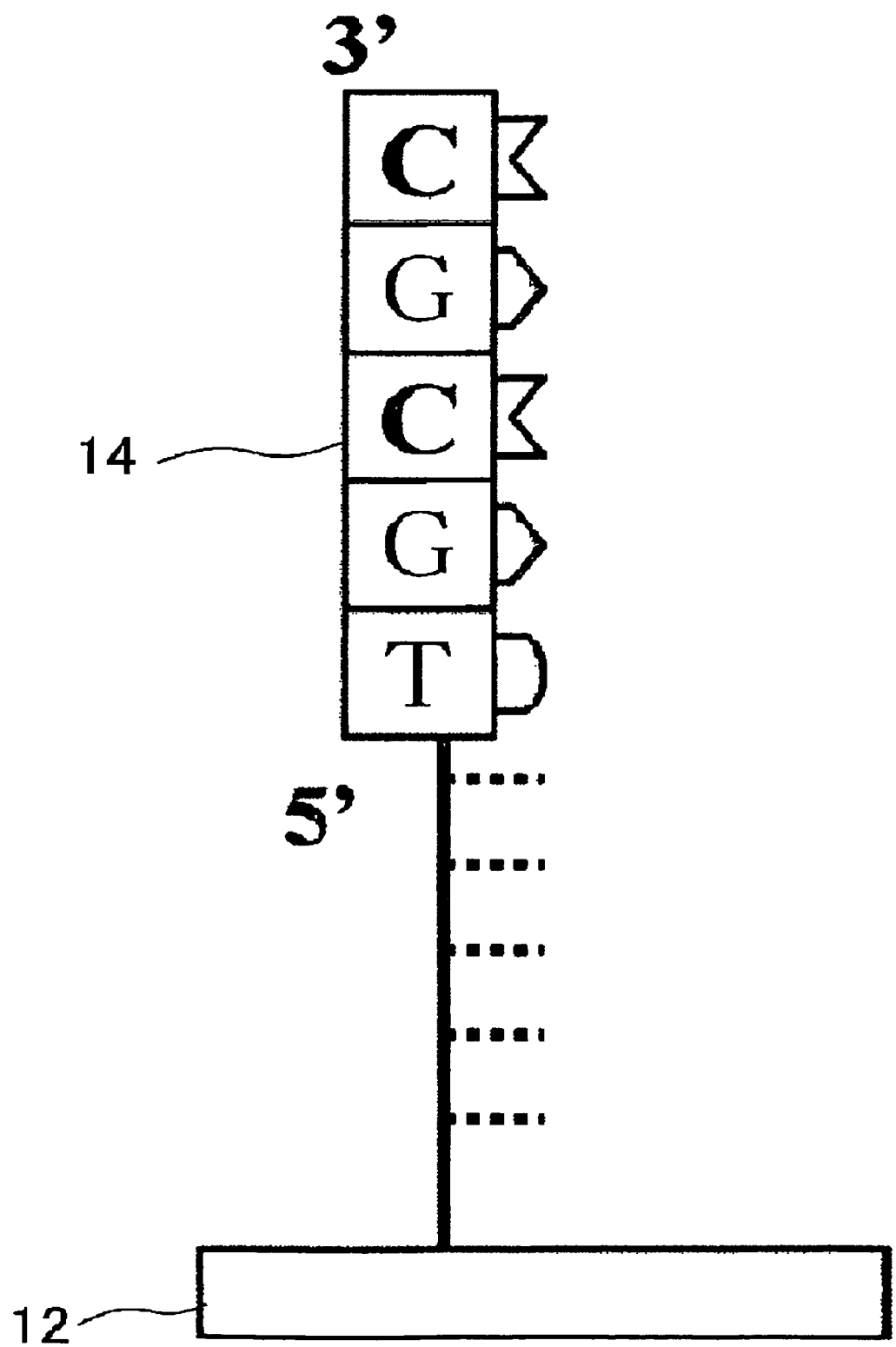

Fig.1-b
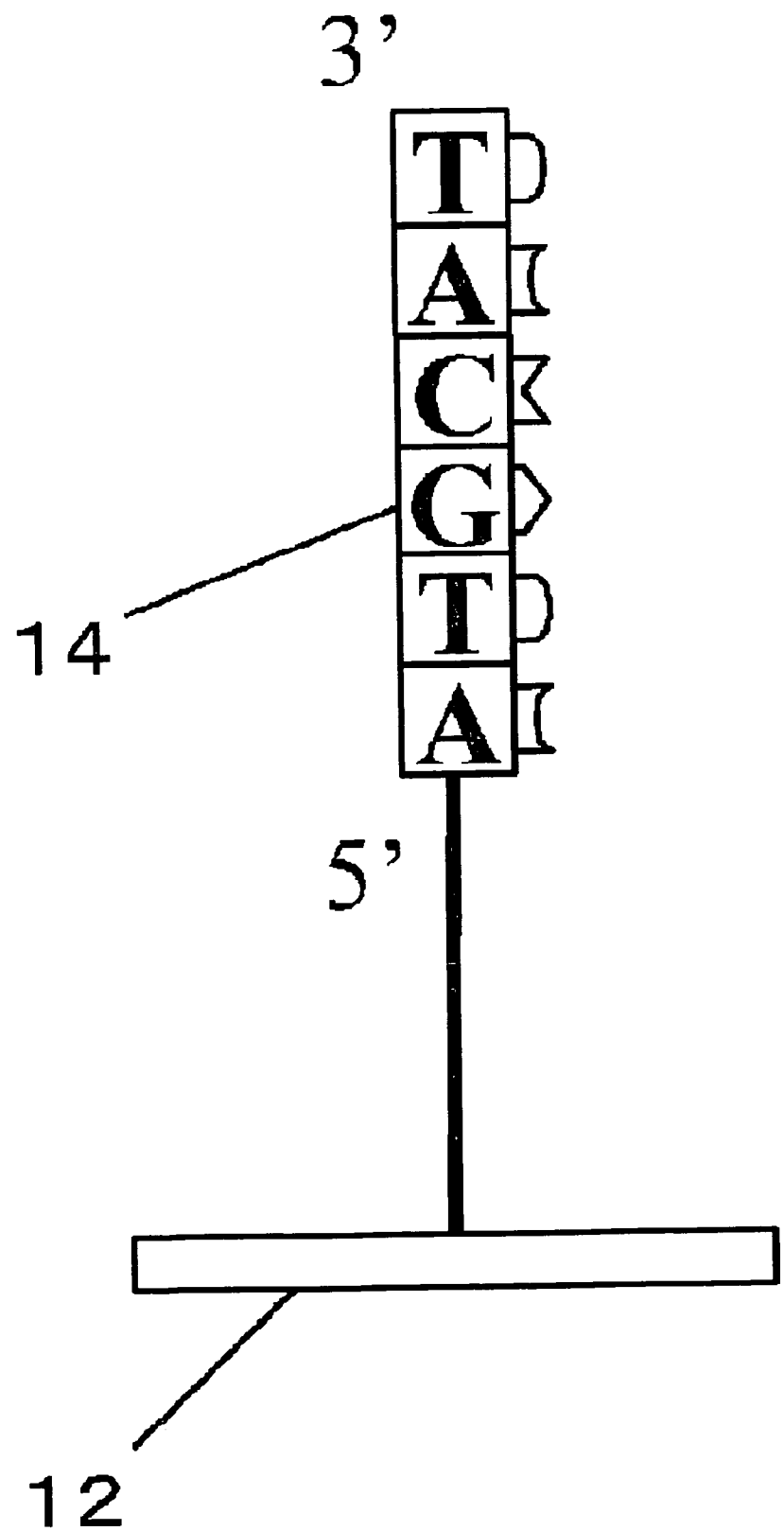

SEQUENCE LISTING

<160> NUMBER OF SEQ ID NOS: 6

<210> SEQ ID NO 1
<211> LENGTH: 28
<212> TYPE: DNA
<213> ORGANISM: Escherichia coli

<400> SEQUENCE: 1
cgagcaagtc gcttcaccta catatcag                                        28

<210> SEQ ID NO 2
<211> LENGTH: 25
<212> TYPE: DNA
<213> ORGANISM: Staphylococcus aureus

<400> SEQUENCE: 2
aatcgcacgc ttcgcctatc ctact                                           25

<210> SEQ ID NO 3
<211> LENGTH: 26
<212> TYPE: DNA
<213> ORGANISM: Pseudomonas aeruginosa

<400> SEQUENCE: 3

-continued

```
aaccgactaa ccctgcgtcg attaac                                          26

<210> SEQ ID NO 4
<211> LENGTH: 30
<212> TYPE: DNA
<213> ORGANISM: Artificial Sequence
<220> FEATURE:
<223> OTHER INFORMATION: Designed DNA probe for synthesis for DNA

<400> SEQUENCE: 4
tttttttttt tttttttttt  tttttttttt                                     30

<210> SEQ ID NO 5
<211> LENGTH: 20
<212> TYPE: DNA
<213> ORGANISM: Artificial Sequence
<220> FEATURE:
<223> OTHER INFORMATION: Designed origonucleotide based on Beta-actin
      gene

<400> SEQUENCE: 5
actggaacgg tgaaggtgac                                                 20

<210> SEQ ID NO 6
<211> LENGTH: 20
<212> TYPE: DNA
<213> ORGANISM: Artificial Sequence
<220> FEATURE:
<223> OTHER INFORMATION: Designed origonucleotide based on Beta-actin
      gene

<400> SEQUENCE: 6
cagtgtacag gtaagccctg                                                 20
```

RNA DETECTION METHOD

This Application is the U.S. National Stage Application under 35 U.S.C. 371 of International Application PCT/JP/2007/000592 filed Jun. 1, 2007, not in English, which claims benefit from Japanese Patent Application No. 2006-159097 filed Jun. 7, 2006, and which claims benefit from Japanese Patent Application No. 2006-258266, filed 25 Sep. 2006.

TECHNICAL FIELD

The present invention relates to an RNA detection method detecting an RNA chain in a sample, using a carrier having a primer DNA chain immobilized on the surface thereof.

BACKGROUND ART

Patent Document 1 describes a technique of allowing solid-phase amplification of a target polynucleotide to proceed, using an oligonucleotide primer immobilized on a solid-phase support. There is further disclosed that a single-strand or double-stranded DNA, and RNA may be adoptable as the target polynucleotide, and that in particular mRNA may directly be adoptable as a template for amplification as being mediated by reverse transcription.

Patent Document 2 discloses a technique of allowing PCR reaction to proceed, by using a microplate which is stable even in a heat denaturation step of the PCR reaction, shows a small capacity of non-specific adsorption of proteins and DNA/RNA, and is durable to organic chemical substances. There is also described that, prior to the PCR reaction, by using an oligonucleotide immobilized on the surface of the microplate, RNA or mRNA may be captured from a crude cell lysate without purification.

In both of Patent Documents 1 and 2, there are described that presence of RNA in the cell lysate may be known, and that the RNA may approximately be quantified, by labeling and detecting the oligonucleotide in the process of amplification.

Specifically for this sort of RNA quantification, reverse transcription-polymerase chain reaction (RT-PCR: reverse transcriptase polymerase chain reaction) has been known to be useful. More specifically, the RT-PCR method, characterized by converting RNA into complementary DNA (cDNA) using a reverse transcriptase, and then amplifying the cDNA by the PCR method, is capable of quantitatively analyzing even a trace amount of RNA, and is now recognized as one of analytical methods having highest detection sensitivity, indispensable for detection of virus having RNA as a gene, quantitative detection of mRNA, analysis of expressive gene based on determination of base sequence, and analysis and production of expression product obtained by cloning of cDNA. The method is a very important technique in various fields including diagnostic molecular pathology.

However, the RT-PCR method is much labor-consuming in collection of cells, extraction of RNA from biological samples and purification thereof, reverse transcription reaction, PCR and gene detection, each of these steps suffers from problems of sample loss, contamination and so forth, so that the current situation is such as needing advanced skills of researchers for the purpose of stable quantification on the gene expression level. In particular, complete purification of RNA molecules is the first step determining success of RT-PCR, so that operations required therefor include removal or inactivation of ribonuclease in the cells and tissues.

To solve these problems, there have been active efforts of developing products such as automatic RNA extraction apparatus, mRNA purification kit, one-step RT-PCR reagent kit, and so forth. For example, the reagents having been used include ion exchange resin, glass filter, glass beads or those showing protein aggregating function. However, use of any of these products needs time-consuming and difficult treatment operation steps.

There has generally been used a purification-oriented technique, by which oligo dT is immobilized on the surface of the carrier, so as to capture a poly-A chain owned by mRNA. The technique was developed for the purpose of further allowing the reverse transcription reaction and the PCR reaction to proceed on the solid-phase surface (Non-Patent Document 1). However, the technique has failed in achieving a satisfactory performance, due to non-specific adsorption on the hydrophobic surface of plastic, raising problems in contamination of a protease or chaotropic reagent used for inactivating ribonuclease, and inactivation of reverse transcriptase and DNA synthase.

[Patent Document 1] Published Japanese Translation of PCT International Publication for Patent Application No. 2003-523183
[Patent Document 2] Published Japanese Translation of PCT International Publication for Patent Application No. 2002-505080
[Non-Patent Document 1] Takashi Ishikawa et al., "Construction of cDNA bank from biopsy specimens for multiple gene analysis of cancer", Clinical Chemistry, 1997, Vol. 43, No. 5, 764

DISCLOSURE OF THE INVENTION

The present inventors went through RNA detection making use of the DNA chain extension reaction based on the MPEC (Multiple Primer Extension on a Chip) method using various substrates exemplified by Patent Documents 1, 2 and so forth, only to find that they were insufficient in the sensitivity, but then solved the problems by using a carrier having a predetermined polymer substance provided on the surface thereof, to thereby complete the present invention.

From another point of view, the present inventors also found out that, in the RNA detection reaction making use of the DNA chain extension reaction, RNA remained after reverse transcription reaction from RNA to cDNA may be causative of a problem of inhibition of the DNA chain extension reaction, and finally completed the present invention, after solving the problem by using a carrier having a predetermined polymer substance provided on the surface thereof.

According to the present invention, there is provided an RNA detection method detecting, from a reaction system containing a target sample, a target RNA chain originated from the target sample, using a surface having thereon a polymer substance which contains a first unit having a group derived from a phosphate ester composing the hydrophilic portion of a phospholipid and a second unit having a carboxylic acid derivative group composed of an electron-attractive substitutional group bound to a carbonyl group, while being provided with at least one reaction space, the reaction space having an immobilized nucleic acid primer immobilized therein.

This sort of surface may be exemplified by the surface of a carrier on which an immobilized DNA primer is immobilized. The reaction space may have a form of a PCR tube, a PCR microplate, or a tube or a well.

According to the present invention, the RNA detection method capable of rapid multi-sample treatment may be provided.

From another viewpoint, RNA may be detected and quantified from a target sample, which is specifically a sample of cell lysate of target cells, in a highly sensitive manner.

From still another viewpoint, in detection of RNA from a target sample while making use of the DNA chain extension reaction, RNA may be detected and quantified in a simple and rapid manner, without including a step of decomposing RNA.

BRIEF DESCRIPTION OF THE DRAWINGS

The above and other objects, advantages and features of the present invention will be more apparent from the following description of certain preferred embodiments taken in conjunction with the accompanying drawings.

FIG. 1-a A drawing schematically showing a part of a substrate as one example of a surface providing a reaction space used in an embodiment of the present invention.

FIG. 1-b A drawing schematically showing a part of a substrate as another example of a surface providing a reaction space used in an embodiment of the present invention.

BEST MODES FOR CARRYING OUT THE INVENTION

Figure 2:
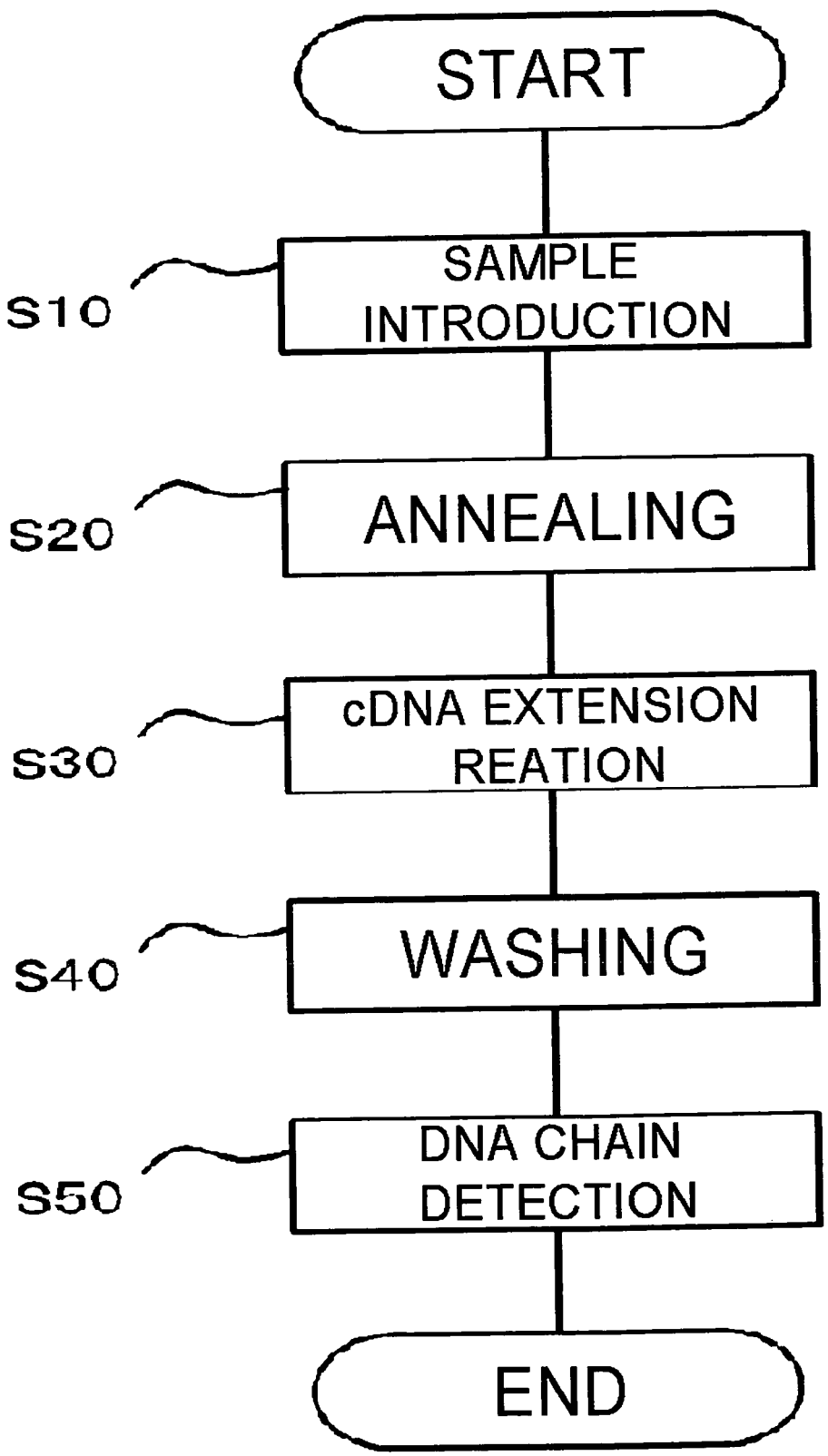
FIG. 2 A flow chart showing an RNA detection method according to a first embodiment.

Embodiments of the present invention will be detailed below.

The RNA detection method according to this embodiment is such as detecting, from a reaction system containing a target sample, a target RNA chain originated from the target sample, using a surface having thereon a polymer substance which contains a first unit having a group derived from a phosphate ester composing the hydrophilic portion of a phospholipid and a second unit having a carboxylic acid derivative group composed of an electron-attractive substitutional group bound to a carbonyl group, while being provided with at least one reaction space, the reaction space having an immobilized nucleic acid primer immobilized therein.

The surface of the substrate applicable to this embodiment allows a polymer substance, which contains a first unit having a group derived from a phosphate ester composing the hydrophilic portion of a phospholipid and a second unit having a carboxylic acid derivative group composed of an electron-attractive substitutional group bound to a carbonyl group, to reside thereon.

The polymer substance, which contains a first unit having a group derived from a phosphate ester composing the hydrophilic portion of a phospholipid and a second unit having a carboxylic acid derivative group composed of an electron-attractive substitutional group bound to a carbonyl group, is a polymer having both of a property of suppressing non-specific adsorption of DNA chain and a property of immobilizing the DNA chain. In particular, the group, derived from a phosphate ester composing the hydrophilic portion of a phospholipid contained in the first unit, plays a role of suppressing non-specific adsorption of a template RNA fragment, and the carboxylic acid derivative group contained in the second unit plays a role of chemically immobilizing a primer. That is, the primer is immobilized to the surface, by forming a covalent bond at the portion of the carboxylic acid derivative group of a coated layer composed of the polymer substance. This sort of surface may be exemplified by a carrier having an immobilized DNA primer immobilized thereon, and typically by the surface of a substrate.

The first unit may typically have a group exemplified by (meth)acryloyloxyalkyl phosphorylcholine groups such as 2-methacryloyloxyethyl phosphorylcholine group, and 6-methacryloyloxyhexyl phosphorylcholine group;

(meth)acryloyloxyalkoxyalkyl phosphorylcholine groups such as 2-methacryloyloxyethoxyethyl phosphorylcholine group, and 10-methacryloyloxyethoxynonyl phosphorylcholine group; and alkenyl phosphorylcholine groups such as allyl phosphorylcholine group, butenyl phosphorylcholine group, hexenyl phosphorylcholine group, octenyl phosphorylcholine group, and decenyl phosphorylcholine group;

and may be configured as containing therein phosphorylcholine group.

Of these groups, 2-methacryloyloxyethyl phosphorylcholine is preferable. By configuring the first unit as having 2-methacryloyloxyethyl phosphorylcholine, non-specific adsorption of the template RNA fragment on the surface of the carrier or the like may more exactly be suppressed.

While the basic skeleton exemplified herein is phosphorylcholine group expressed by the formula (a) below, the phosphorylcholine group may be replaced by any of phosphoric acid group such as phosphorylethanolamine group expressed by the formula (b) below, phosphorylinositol group expressed by the formula (c) below, phosphorylserine group expressed by the formula (d) below, phosphorylglycerol group expressed by the formula (e) below, and phosphatidyl phosphorylglycerol group expressed by the formula (f) below (the same will apply also hereinafter).

(Formula 1)

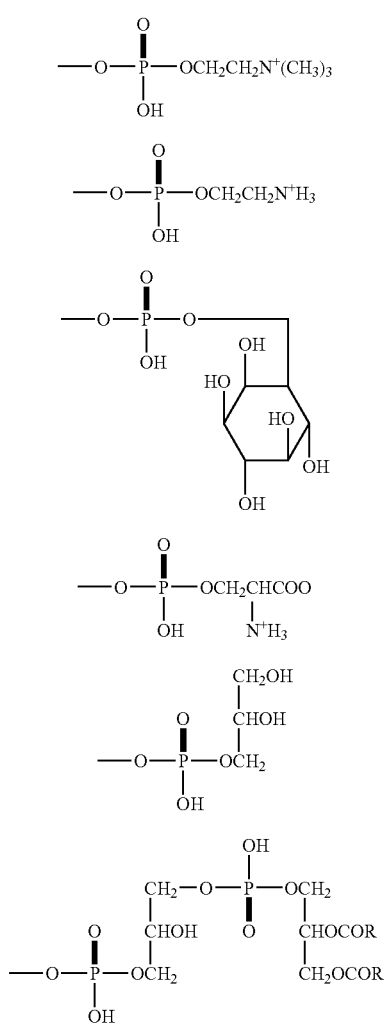

(a)

(b)

(c)

(d)

(e)

(f)

The carboxylic acid derivative is such as having the carboxyl group activated therein, and is a carboxylic acid having a leaving group bound to C=O. The carboxylic acid derivative is specifically a compound more enhanced in nucleophilic reactivity, by virtue of a group, having electron attractive property larger than that of alkoxyl group, bound to the carbonyl group. The carboxylic acid derivative group is a compound showing reactivity with amino group, thiol group, hydroxyl group and so forth.

The activated carboxylic acid derivative may further specifically be exemplified by compounds having carboxyl groups of carboxylic acid, such as acrylic acid, methacrylic acid, crotonic acid, maleic acid, fumaric acid and so forth, converted to acid anhydride, acid halide, activated ester or activated amide. The carboxylic acid derivative group is an activated group originated from such compounds, and may typically have a group such as activated ester groups exemplified by p-nitrophenyl group, N-hydroxysuccinimide group and so forth; and halogens such as —Cl, —F and so forth.

Incidentally, the carboxylic acid derivative group may be a group expressed by the formula (1) below:

(Formula 2)

 (1)

(where, in the formula (1) in the above, "A" represents a leaving group excluding hydroxyl group.) The monovalent group expressed by the formula (1) in the above may be any group selected typically from those expressed by the formula (p) or formula (q) below:

(Formula 3)

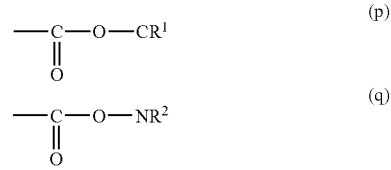

(p)

(q)

(where, in the formula (p) and the formula (q), each of $R^1$ and $R^2$ independently represents a monovalent organic group, and may have any of straight-chain, branched and cyclic form. In the formula (p) in the above, $R^1$ may be a divalent group capable of forming a ring together with C. In the formula (q) in the above, $R^2$ may be a divalent group capable of forming a ring together with N.)

As the groups expressed by the formula (p) in the above, those expressed by the formulae (r), (s) and (w) below may be exemplified. On the other hand, as the groups expressed by the formula (q) in the above, those expressed by the formula (u) below may be exemplified.

The group expressed by the formula (1) in the above may typically be groups originated from acid anhydrides expressed typically by the formula (r) and the formula (s) below;

groups originated from acid halides expressed by the formula (t) below;

groups originated from activated esters expressed by the formula (u) and the formula (w) below; or groups originated from activated amides expressed by the formula (v) below:

(Formula 4)

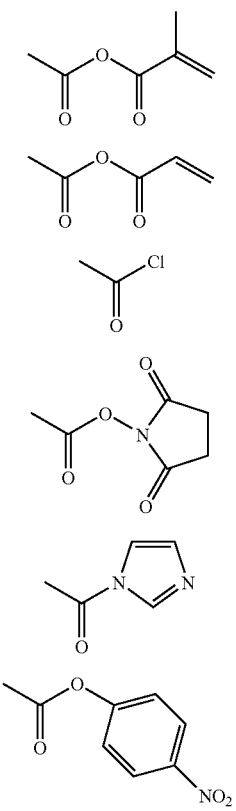

Of the carboxylic acid derivative group, the activated ester group may preferably be used, by virtue of its excellent reactivity under a mild condition. The mild condition may be a neutral or alkaline condition, and more specifically having pH7.0 or above and 10.0 or below, more specifically pH7.6 or above and 9.0 or below, and still more specifically pH8.0.

The "activated ester group" specified in this specification, while being not strictly specified, has generally been used as a general technical term in the fields of various chemical syntheses, including polymer chemistry and peptide synthesis, indicating an ester group capable of enhancing nucleophilic reactivity by virtue of having a highly acidic electron-attractive group on the alcoholic side of the ester group, and in short, a highly reactive ester group. Incidentally, in the field of peptide synthesis, the activated ester method is used as one method of activating the C-terminal of amino acid or peptide, as described by Nobuo Izumiya, Tetsuo Kato, Haruhiko Aoyagi and Michinori Waki, "Pepuchido Gosei no Kiso to Jikken (Basics and Experiments of Peptide Synthesis)", 1985, Maruzen.

On the practical basis, it is an ester group having an electron attractive group on the alcoholic side thereof, thereby further activated than alkyl ester. The activated ester group shows reactivity with groups including amino group, thiol group and hydroxyl group. Still more specifically, phenol esters, thiophenol esters, N-hydroxyamine esters, cyanomethyl esters, and esters of heterocyclic hydroxy compounds have been known as the activated ester groups showing far higher activity than that of alkyl esters or the like.

In this specification, explanation will be made on an exemplary case where the activated carboxylic acid derivative group in the polymer substance is the activated ester group. The activated ester group may be exemplified by p-nitrophenyl group, N-hydroxysuccinimide group, succinimide group, phthalic imide group, and 5-norbornene-2,3-dicarboxyimide, wherein p-nitrophenyl group may preferably be used.

As for the carrier, such as a substrate, having a primer immobilized on the surface thereof, more specific combination of configuration of the first unit and the second unit may be exemplified by a configuration in which the first unit containing a group derived from a phosphate ester composing the hydrophilic group of a phospholipid has 2-methacryloyloxyethyl phosphorylcholine group, and the activated ester group is p-nitrophenyl group.

The polymer substance used for a coated layer of the carrier such as a substrate adoptable to this embodiment may include a group other than the group derived from a phosphate ester composing the hydrophilic portion of a phospholipid and carboxylic acid derivative group. The polymer substance may be a copolymer. More specifically, the polymer substance may preferably be a copolymer containing a butyl methacrylate group. By adopting this configuration, the polymer substance may appropriately be made hydrophobic, and thereby adhesiveness of the polymer substance onto the surface of the polymer substance may be ensured to a more preferable degree.

More specifically, the polymer substance may be a copolymer composed of a first monomer having 2-methacryloyloxyethyl phosphorylcholine (MPC) group, a second monomer having p-nitrophenyloxycarbonyl polyethylene glycol methacrylate (NPMA) group, and a third monomer having butyl methacrylate (BMA) group. A copolymer of these monomers poly(MPC-co-BMA-co-NPMA) (PMBN) is schematically expressed by the general formula (2) below:

(Chemical Formula 5)

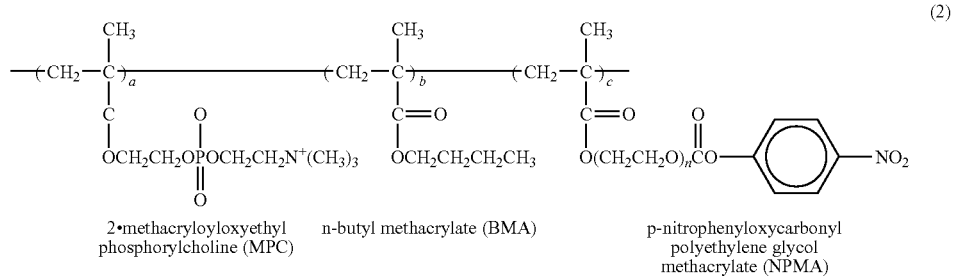

Where, in the general formula (2) in the above, each of "a", "b", and "c" independently represents a positive integer. In the general formula (2) in the above, the first to third monomers may form a block copolymer, or these monomers may form a random copolymer.

The copolymer expressed by the general formula (2) in the above has a configuration further well balanced among appropriate hydrophobicity of the polymer substance, property of suppression of non-specific adsorption of template RNA fragments, and property of immobilizing the primer. As a consequence, by using this sort of copolymer, the carrier such as a substrate may more reliably be covered with the polymer substance, and the primer may be introduced to the carrier by more reliably immobilizing it by a covalent bond, while suppressing non-specific adsorption of template RNA fragment onto the carrier coated with the polymer substance.

The copolymer expressed by the general formula (2) in the above may be obtained by any of publicly-known methods of polymerization such as radical polymerization, while mixing the individual monomers of MPC, BMA and NPMA. For the case where the copolymer expressed by the general formula (2) in the above is prepared by radical polymerization, solution polymerization may be proceeded in an atmosphere of inert gas such as Ar, under a temperature condition of 30° C. or above and 90° C. or below.

Solvent used for the solution polymerization may appropriately be selected, wherein alcohols such as methanol, ethanol and isopropanol, ethers such as diethyl ether, and organic solvents such as chloroform may be used independently or by mixing a plurality of them. More specifically, an 8:2 mixed solvent of diethyl ether and chloroform on the volume basis may be used.

Radical polymerization initiator used for the radical polymerization reaction may be any of those generally used. For example, azo initiators such as azobis(isobutyronitrile) (AIBN) and azobis(valeronitrile); and oil-soluble organic peroxides such as lauroyl peroxide, benzoyl peroxide, t-butylperoxy neodecanoate and t-butylperoxy pivalate are adoptable.

Still more specifically, using an 8:2 mixed solution of diethyl ether and chloroform on the volume basis and AIBN, the polymerization may be proceeded in Ar, at 60° C. for approximately 2 to 6 hours.

The carrier such as a substrate applicable to this embodiment, having been explained herein, was such that the polymer substance has the third unit containing a butyl methacrylate group, wherein a polymer substance having a first unit containing a group derived from a phosphate ester composing the hydrophilic portion of a phospholipid, and a second unit containing a carboxylic acid derivative group may be assumed as a first polymer substance, and in addition to this, a second polymer substance having a first unit containing a group derived from a phosphate ester composing the hydrophilic portion of a phospholipid, and a third unit containing a butyl methacrylate group, may be contained.

The first unit in the first polymer substance and the first unit in the second polymer substance may have the same structure, or may have different structures. For the case where the first polymer substance contains the third unit containing a butyl methacrylate group, the third unit of the first polymer substance and the third unit of the second polymer substance may have the same structure, or may have different structures.

This sort of second polymer substance may be used as a polymer suppressing non-specific adsorption of template RNA fragment. As this sort of polymer, MPC polymer (from NOF Corporation), containing phosphorylcholine group at a ratio of 30 mol %, and butyl methacrylate group at a ratio of 70 mol %, may typically be used.

For the case where the polymer substance is composed of the first polymer substance and the second polymer substance, these polymer substances may be mixed. Because polymers composing the individual polymer substances are soluble for example to ethanol, the mixed polymer may readily be obtained by mixing the individual polymer solutions.

The carrier having the coated layer composed of the above-described polymer substance on the surface thereof may be obtained by spreading a solution containing the polymer substance onto the carrier, such as a substrate, processed to a predetermined geometry, and then drying it. Incidentally, the carrier may be immersed in the solution containing the polymer substance, and then dried.

Use of a plastic material as the carrier may be preferable, from the viewpoints of ensuring flexibility to geometrical or dimensional modification, and of possibly providing the carrier at lower cost as compared with glass carrier. In particular for the case where a substrate is adopted as the carrier, and a plastic is adopted as the material, the geometry is not limited to plate-like, but may be film-like or sheet-like. More specifically, the substrate may be a flexible plastic film. The substrate may be composed of a single component, or a plurality of components.

As the plastic material, a thermoplastic resin may be used from the viewpoint of readiness in surface treatment and mass producibility.

As the thermoplastic resin, those causative of only a small emission of fluorescence may be adoptable. By using the resins causative of only a small emission of fluorescence, the background level of reaction for detecting DNA chain may be lowered, and thereby the detection sensitivity may further be improved. As the thermoplastic resins causative of only a small emission of fluorescence, straight-chain polyolefins such as polyethylene and polypropylene;

cyclic polyolefin;

fluorine-containing resin; and styrene; may typically be used. Of these resins described in the above, saturated cyclic polyolefin is suitable for optical analysis by virtue of its excellence in heat resistance, chemical resistance, low fluorescent emission, transparency and moldability, and is preferably used as a material composing the substrate.

The saturated cyclic polyolefin herein means a saturated polymer obtained by hydrogenation of a homopolymer having a cyclic olefin structure, or a copolymer of cyclic olefin and α-olefin. The former may be exemplified by a saturated polymer, manufactured by hydrogenating a polymer obtained by ring-opening polymerization of norbornene monomers represented by norbornene, dicyclopentadiene and tetracyclododecene, and alkyl substituted products of them. The latter copolymer may be exemplified by a saturated polymer, manufactured by hydrogen addition of a random copolymer of an α-olefin such as ethylene, propylene, isopropylene, 1-butene, 3-methyl-1-butene, 1-pentene, 3-methyl-1-pentene, 1-hexene or 1-octene, with a cyclic olefin monomer. As the copolymer, those copolymerized with ethylene are most preferable. These resins may be used independently, or they may be copolymers or mixtures of two or more species. Not only saturated cyclic polyolefins obtained by ring-opening polymerization of monomers having cyclic olefin structures, but also saturated cyclic polyolefins obtained by addition polymerization of monomers having cyclic olefin structures may be used.

As for geometry of the reaction space of the carrier, microtube, microtube dedicated for PCR or quantitative PCR, microtiter plate of 96-well, 384-well or 1536-well-type may be used. Incidentally, also a plate-type plastic surface may be used. Still, an inner space of a micro fluid passageway formed in the carrier by fine processing may be used. In particular, the microtube dedicated for PCR or quantitative PCR, having a small thickness of container, may preferably be used in view of controllability of reaction temperature by a PCR reaction device.

Next, a method of immobilizing the immobilized nucleic acid primer (referred to as "primer", hereinafter) onto the surface which provides a reaction space will be explained, referring to an exemplary case of immobilizing the primer onto the surface of the carrier. The primer herein may be exemplified by DNA primer, RNA primer, LNA (locked nucleic acid) primer, and ENA® (2'-O,4'-C-Ethylene-bridged Nucleic Acids) primer.

For example, (i) the primer is immobilized onto the surface of the carrier, by allowing at least a part of activated ester groups out of a plurality of activated ester groups contained in the polymer substance on the carrier, to react with the primers to thereby form covalent bonds, and succeedingly (ii) the activated ester group primers on the carrier, other than those having the primers immobilized thereon, are inactivated. In other words, by inactivating the residual activated ester groups, the primers may be immobilized on the surface of the carrier. The individual steps will be explained below.

In the step (i), when the primers to be annealed with template RNA fragments are immobilized onto the carrier, a liquid having the primers dissolved or dispersed therein is brought into contact (or spotted), wherein a part of the activated ester groups contained in the polymer substance react with the primers, to thereby form the covalent bonds with the primers. Incidentally, in place of bringing the liquid having the primers dissolved or dispersed therein into contact with the surface of the carrier, a micro array design may be obtained by spotting the liquid.

The liquid having the primers dissolved or dispersed therein may be adjusted to neutral to alkaline, and typically to pH 7.6 or above.

The carrier may be washed with pure water or a buffer solution after the contact (or spotting), in order to remove the primers not immobilized onto the surface of the carrier.

As shown in the step (ii), after the washing, the activated esters on the surface of the plastic carrier, other than those having the primers immobilized thereon, are inactivated using an alkaline compound or a compound having primary amino group.

As the alkali compound, sodium hydroxide, potassium hydroxide, sodium carbonate, sodium hydrogen carbonate, disodium hydrogen phosphate, calcium hydroxide, magnesium hydroxide, sodium borate, lithium hydroxide, potassium phosphate or the like may be adoptable.

As the compound having primary amino group, glycine, 9-aminoacridine, aminobutanol, 4-aminobutyric acid, aminocaprylic acid, aminoethanol, 5-amino-2,3-dihydro-1,4-pentanol, aminoethanethiol hydrochloride, aminoethanethiol sulfate, 2-(2-aminoethylamino)ethanol, 2-aminoethyl dihydrogen phosphate, aminoethyl hydrogen sulfate, 4-(2-aminoethyl)morpholine, 5-aminofluorescein, 6-aminohexanoic acid, aminohexyl cellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, aminosalicylic acid, aminoquinoline, 4-aminophthalonitrile, 3-aminophthalimide, p-aminopropiophenone, aminophenylacetic acid, aminonaphthalene and so forth may be adoptable. Of these, aminoethanol and glycine may preferably be used.

It may be preferable that the primer to be immobilized onto the carrier are preliminarily be introduced with an amino group, in order to enhance reactivity with the activated ester group. The amino group is excellent in reactivity with the activated ester group, so that by using the primer introduced with the amino group, the primer may be immobilized onto the surface of the carrier in an efficient and tight manner. Position of introduction of amino group may be the end of, or side chain of the molecular chain of the primer, wherein introduction at the end of the molecular chain may be preferable, from the viewpoint of allowing annealing with complementary template RNA fragment to proceed in a further efficient manner.

In this way, the carrier having the primers immobilized on the surface thereof, adoptable to this embodiment, may be obtained. The carrier 12 has, as shown in FIG. 1-a and FIG. 1-b, a primer 14 immobilized on the surface thereof. The reaction space provided over the surface of the carrier 12 may have any geometry such as tube, well, liquid passageway and so forth, so far as it can provide a reaction space allowing extension reaction of DNA chain to proceed therein. For the purpose of detection based on quantitative PCR, a tube geometry with a transparent lid, for example, adapted to a real time PCR device, may be preferable. Length of the primer 14 may arbitrarily be determined depending on purposes and applications, typically to as long as 5 to 50 bases.

The carrier having the primer immobilized thereon obtained as described in the above may be suppressed in non-specific adsorption onto the surface of the carrier, as compared with general plastic surfaces, by virtue of effect of hydrophilic groups of the polymer. Accordingly, only RNA and DNA complementary to the primer immobilized onto the surface thereof may be captured from a target sample which is typically a sample containing, as being mixed therein, components of biological origin such as cell lysate of target cells, and thus-captured RNA and DNA may be purified by removing the supernatant, followed by washing. General plastic surface cannot achieve thorough purification due to non-specific adsorption, because also substances other than the captured RNA and DNA may be adsorbed by the surface. As a consequence, the non-specific adsorption adversely affects quantitative detection.

The hydrophilic group composing the polymer has phosphorylcholine group assimilating cell surface, and therefore never inhibits enzyme reaction on the surface of solid. By virtue of this effect, the reverse transcription reaction may effectively be proceeded using the captured mRNA as a template, to thereby prepare a solid-phase cDNA. By further proceeding the quantitative PCR reaction using the solid-phase cDNA as a template, mRNA contained in the starting material may be quantified.

In general, methods of purifying RNA such as those relying upon a method of extraction using an organic solvent, or purification using magnetic beads suffer from labor-consuming steps, and need operation by a highly-skilled operator. Moreover, anticipation of loss of mRNA in the purification step, and contamination of RNase or during sample transfer may raise a need of a large amount of sample as a starting material, and a large variation in efficiency of purification may raise a need of quantification of RNA for every purified product using a spectrophotometer. In contrast, according to the RNA detection method of the present invention, purification of mRNA from cell lysate by a simple operation, reverse transcription reaction, and PCR reaction may be proceeded in the same reaction solution, so that the steps necessary in the conventional method may be omissible, risks of loss of mRNA in the process of purification and contamination of RNase or during sample transfer may be reduced, and RNA may rapidly be detected. As a consequence, RNA may be quantified only from a small amount of starting material.

The liquid-phase cDNA may be prepared using the mRNA captured on the solid phase as a template, by adding a reverse transcription reaction solution containing a random primer to the reaction space having only RNA and DNA complementary to the primer immobilized onto the surface. Moreover, by amplifying DNA or RNA by the PCR reaction using the liquid-phase cDNA, mRNA may be quantified using the amplified DNA or RNA. This sort of techniques of amplifying DNA or RNA may be exemplified typically by the PCR method, LAMP (Loop-mediated Isothermal Amplification) method, NASBA (Nucleic Acid Sequence-Based Amplification) method, TRC (Transcription Reverse transcription Concerted Reaction) method and so forth.

In this embodiment, an array having a plurality of reaction spaces independent from each other may be configured on the carrier. The individual reaction spaces herein may respectively immobilize the immobilized nucleic acid primers. By composing the substrate as having such array, a plurality of assays may be proceeded in parallel, making screening accessible.

Specific embodiments of the RNA detection method using the carrier will be explained below.

FIRST EMBODIMENT

FIG. 2 is a flow chart showing procedures of the RNA detection method as a first embodiment. FIG. 3A to FIG. 3C and FIG. 4A to FIG. 4D are drawings schematically showing reaction proceeded in the reaction space of the carrier, according to the flow chart shown in FIG. 2.

The RNA detection method includes a first step introducing a sample 22 which contains a target sample, which is typically cell lysate of target cells, an enzyme system for DNA chain extension, and nucleotide monomers into a reaction space 20 provided on the carrier 12 (substrate, for example) (step S10), and allowing DNA chain extension reaction ahead of the immobilized DNA primer (primer 14) to proceed using an RNA chain 16 contained in the target sample as a template (steps S20, S30); and a second step detecting a DNA chain 18 obtained by the extension reaction (step S50).

Figure 3:
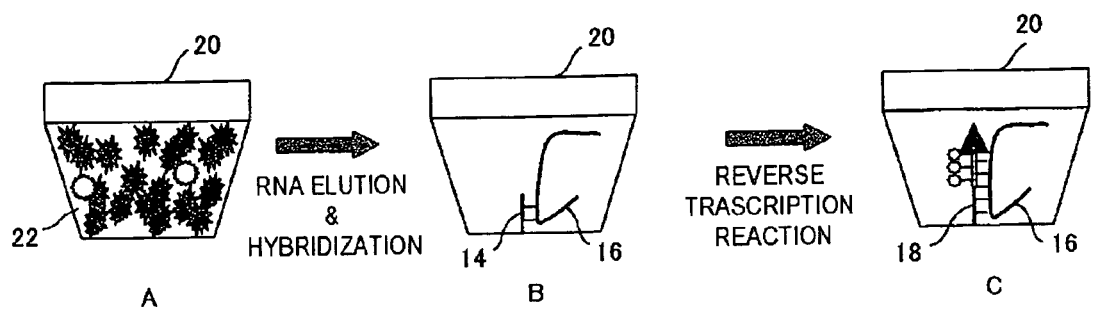
FIG. 3 A drawing schematically showing a reaction takes place in the reaction space of the substrate according to the flow chart shown in FIG. 2.

As shown in FIG. 2, in step S10, the sample 22 containing the cell lysate, the enzyme system for DNA chain extension, and the nucleotide monomers is introduced into the reaction space 20 having the primer 14 immobilized onto the surface of the carrier 12 shown in FIG. 1-a and FIG. 1-b (FIG. 3A). The cell lysate contains the template RNA chain 16 to be annealed with the primer 14 for extending DNA chain (FIG. 4A), wherein any sample containing uncell lysate as shown in FIG. 3A should be used after solubilizing the cells so as to elute RNA.

As the reaction system composed of the sample introduced into the reaction space 20, a buffer for MPEC containing nucleotide monomers (dATP, dCTP, dGTP, dTTP and so forth: dNTP) may be adoptable, under the presence of an enzyme system for DNA chain extension composed of a reverse transcriptase, or a combination of a DNA ligase and a reverse transcriptase.

Incidentally, at least one species of these nucleotide monomers may be labeled. For example, by using Cy™ 3-dUTP, which is a dTTP labeled on the 3-position of base with fluorescence, as a nucleotide monomer, Cy™ 3-dUTP will be inserted at a position on the primer side corresponded to adenine (A) in the template RNA fragment. As a consequence, a DNA fragment produced from the primer, caused thereon the extension reaction, is dyed with fluorescence of Cy™ 3-dUTP, making it possible to detect the DNA fragment.

Incidentally, any of other nucleotide monomers may be labeled, and even a plurality of species of the nucleotide monomers may be labeled. Any other methods of labeling other than introduction of a fluorescent substance, including a method of introducing a photo-absorbing substance, a method of radioactive labeling ($P^{32}$-ATP, $P^{32}$-DATP), a method of enzymatic labeling, may allow detection of DNA chain.

In the method of enzymatic labeling, DNA may be detected by extending the primer using a nucleic acid (biotin-dUTP, DIG-dUTP, for example) bound with biotin or with digoxigenin (DIG: steroidal natural product), to react resulting product with a fluorescence-labeled alkaline phosphatase or with an alkaline phosphatase, and to allow the resulting product to react in a solution containing nitro blue tetrazolium (NBT) and 5-bromo-4-chloro-3-indoryl phosphate (BCIP) for several hours.

Figure 4:
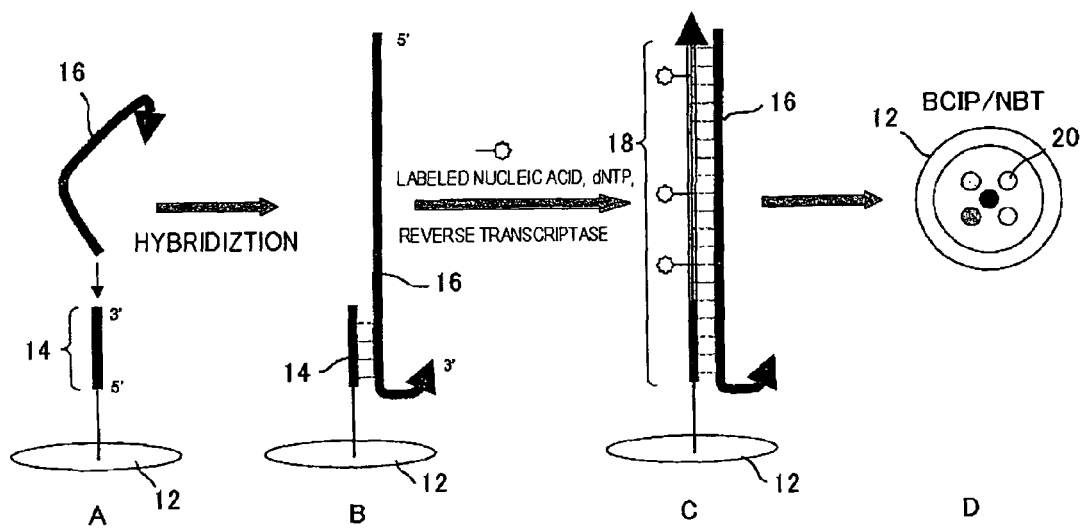
FIG. 4 A drawing schematically showing a reaction takes place in the reaction space of the substrate according to the flow chart shown in FIG. 2.

Referring now back to FIG. 2, in step S20, temperature of the reaction system is kept at a temperature at which the primer 14 and the template RNA chain 16 are annealed (annealing temperature), typically at 4° C. to 65° C., and preferably 50° C. to 65° C. By the annealing, the primer 14 having a sequence complementary to a part of the template RNA chain 16 hybridizes with the RNA chain 16, to thereby form a double strand (FIG. 3B, FIG. 4B). It is to be noted that any primer 14 having no sequence complementary to any portions of the sequence of the RNA chain 16 never forms the double strand. The process may directly advance to step S30, without subjecting the reaction system to any washing for removing unreacted RNA chain remained without forming the double strand.

At this point of time, the above-described washing has conventionally been necessary, after the annealing and before the extension reaction. In this embodiment, washing of the carrier is no more essential, because there are no RNA fragments adsorbed non-specifically onto the carrier, and therefore an enzymatic reaction relevant to the DNA chain extension may take place supposedly in an efficient manner. It may, however, be no problem to advance the process to step P30 after the washing, similarly to as in the conventional process.

In step S30, as shown in FIG. 3C and FIG. 4C, at the 3'-terminal of the primer 14, the reverse transcription reaction takes place with the aid of the enzyme system for DNA chain extension while using the RNA chain 16 as a template, and thereby the extension reaction of DNA chain proceeds. As a consequence, the cDNA chain 18 complementary to the RNA chain 16 is formed on the carrier 12. By allowing the sample 22 to be introduced in step S10 to preliminarily contain the above-described labeled nucleic acid, besides nucleotide monomers (dNTP), the cDNA chain 18 formed on the carrier 12 may be labeled (FIG. 3C, FIG. 4C).

In step S40, the reaction solution is discarded, and the carrier 12 is washed typically using a 0.1 wt % SDS solution.

In step S50, the cDNA chain 18 shown in FIG. 3C and FIG. 4C is detected.

More specifically, fluorometric detection using labeled nucleotide monomers, such as Cy™ 3-dUTP, introduced in step S10, or fluorometric detection using nucleotide monomers introduced with aminoallyl, or fluorometric detection using a biotin-labeled nucleotide monomers reacted with fluorescence-labeled avidin, may be carried out.

Incidentally, state of formation of cDNA chain may be confirmed by visualization, by introducing an enzyme in a form of alkaline phosphatase- or peroxidase-labeled avidin, and allowing chromogenic reaction to proceed using BCIP/NBT reagent, TNBZ or OPD. If alkaline phosphatase is introduced and the BCIP/NBT reagent is used, the reaction spaces having the cDNA chain formed therein may be confirmed as spots, as shown in FIG. 4D. According to the chromogenic reaction using TMBZ or OPD, the degree of formation of cDNA may more exactly be understood, by measuring absorbance using a plate reader.

As shown in FIG. 4D, if a plurality of reaction spaces 20 are provided independently from each other to form an array on the carrier 12, screening may be accessible by varying, for every reaction space 20, reaction conditions, such as types of primer, concentration of the reagents, types of enzyme for DNA chain extension and so forth.

SECOND EMBODIMENT

Figure 5:
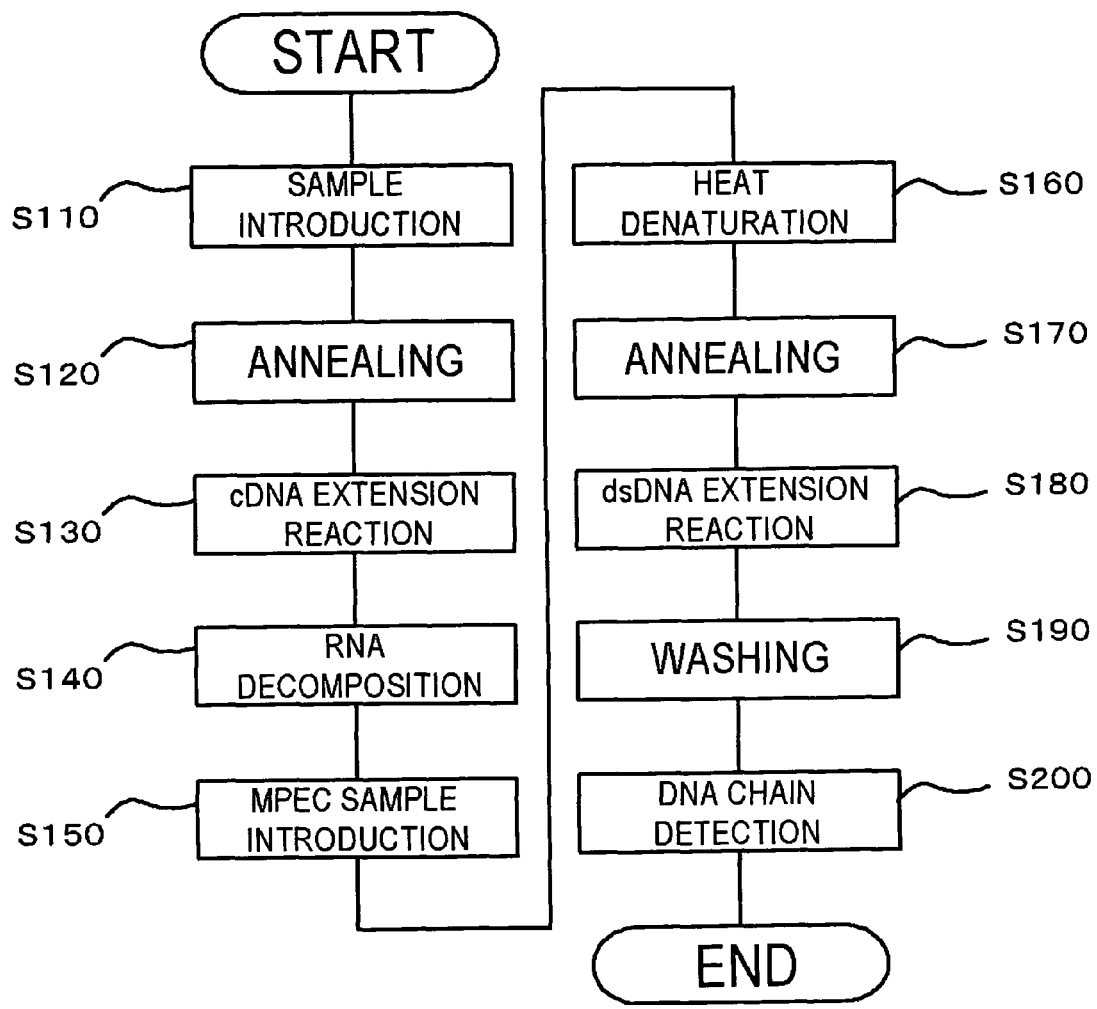
FIG. 5 A flow chart showing an RNA detection method according to a second embodiment.

FIG. 5 is a flow chart showing procedures of the RNA detection method as a second embodiment. FIG. 6A to FIG. 6D and FIG. 7A to FIG. 7E are drawing schematically showing reactions proceeded in the reaction space of the substrate, according to the flow chart shown in FIG. 5.

The RNA detection method includes a first step introducing, into the reaction space 20 provided on the carrier 12, a sample 22 containing the target sample, which is typically cell lysate of target cells, an enzyme system for DNA chain extension and nucleotide monomers (step S110), and allowing a DNA chain extension reaction to proceed ahead of the immobilized DNA primer (primer 14), while using an RNA chain 16 contained in the target sample as a template, to thereby form a cDNA chain 18 (steps S120, S130); a second step decomposing the RNA chain 16 in the reaction system 20, after the DNA chain extension reaction (step S140); a third step introducing, into the reaction system containing the cDNA chain 18, a mixture containing a DNA primer for extension, an enzyme system for DNA chain extension and nucleotide monomers (step S150), and synthesizing a double-strand (ds)DNA 21, while using the cDNA chain 18 as a template (steps S160, S170, S180); and a fourth step detecting the synthesized double-strand DNA 21 (step S200).

Figure 6:
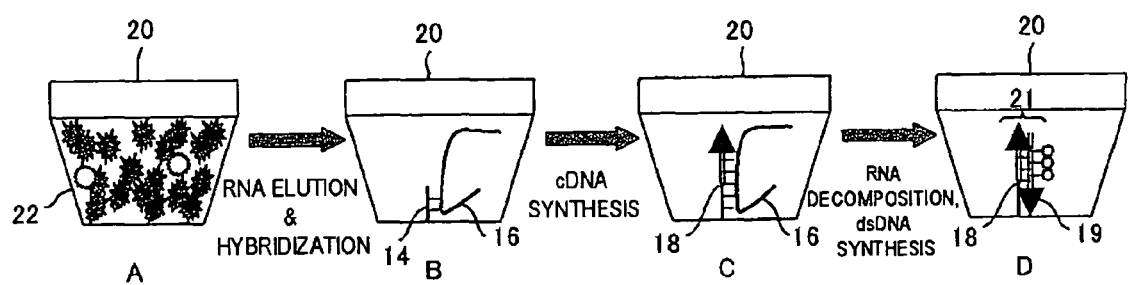
FIG. 6 A drawing schematically showing a reaction takes place in the reaction space of the substrate according to the flow chart shown in FIG. 5.
Figure 7:
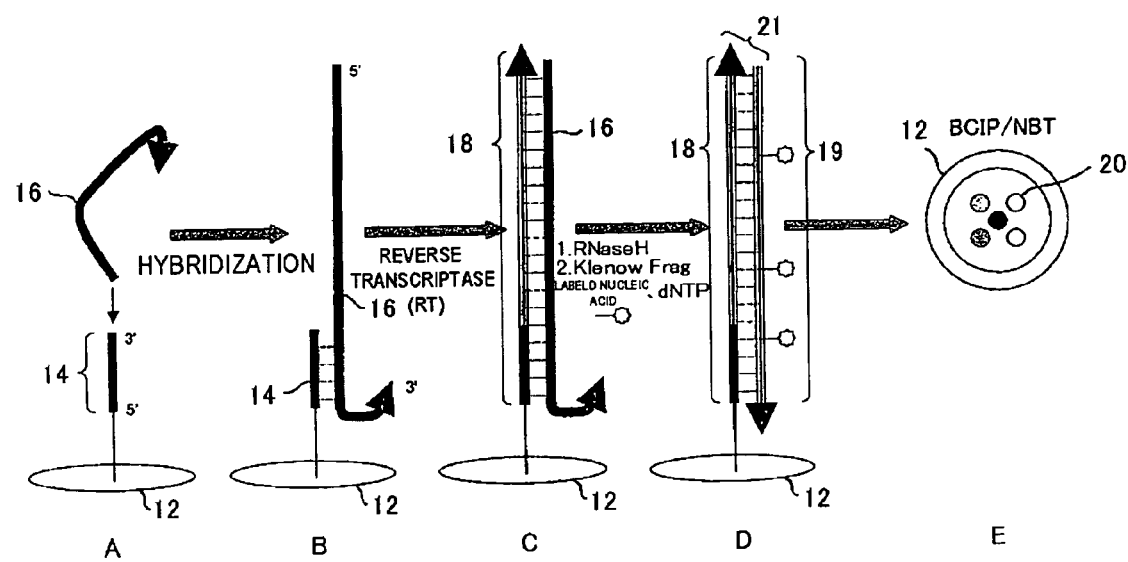
FIG. 7 A drawing schematically showing a reaction takes place in the reaction space of the substrate according to the flow chart shown in FIG. 5.

According to FIG. 5, in step S110, similarly to as in step S10 in FIG. 2, the sample 22 is introduced into the reaction space 20 having the primer 14 immobilized therein (FIG. 6A, FIG. 7A). It has been described in the above that, in FIG. 2, at least one species of nucleotide monomers in the sample introduced into the reaction space 20 may be labeled, whereas in this embodiment, a label is not introduced in the step of extending cDNA chain described later.

In step S120, similarly to as in step S20 in FIG. 2, RNA is eluted, if necessary, from the sample 22 and annealed, so as to hybridize the primer 14 having a sequence complementary to a part of the template RNA chain 16 with such RNA chain 16, to thereby form a double strand (FIG. 6B, FIG. 7B). It is to be noted that, similarly to as in the first embodiment, any primer 14 having no sequence complementary to any portions of the sequence of the RNA chain 16 never forms the double strand.

In step S130, similarly to as in step S30 in FIG. 2, reverse transcription reaction proceeds at the 3'-terminal of the primer 14, while using the RNA chain 16 as a template, under the action of the enzyme system for DNA chain extension, thereby extension reaction of the DNA chain proceeds, and the cDNA chain 18 complementary to the RNA chain 16 is formed on the carrier 12 (FIG. 6C, FIG. 7C).

In step S140, ribonuclease H, specifically decomposing RNA chain contained in RNA-DNA hybrid, is introduced into the reaction system, so as to decompose only the RNA chain 16.

In step S150, an MPEC sample containing a DNA primer for extension (not shown) having a sequence complementary to a part of the cDNA chain 18 as a template DNA chain, an enzyme system for DNA chain extension, and nucleotide monomers (dNTP) is introduced. Klenow fragment, for example, may be exemplified as the enzyme system for DNA chain extension. To the nucleotide monomers, at least one species of which may be introduced with a label, just like the nucleotide monomers introduced in step S10 in FIG. 2.

In step S160, temperature of the reaction system introduced with the sample is elevated to not less than a temperature of heat denaturation (melting temperature: Tm) of DNA chain, typically up to 90° C. to 95° C. By the heat denaturation, the cDNA chain and DNA primer for extension, formed on the carrier, having folded structures such as those observed in self-complementary chain, are converted to straight single strand. The reaction system is directly brought into step S170, without washing.

At this point of time, washing for removing the DNA fragments not brought into double strand has conventionally been necessary, after the annealing and before the extension reaction, whereas in this embodiment, washing of the carrier is no more necessary, because there are no DNA fragments adsorbed non-specifically onto the carrier, and therefore an enzymatic reaction relevant to the DNA chain extension may take place supposedly in an efficient manner. In contrast to the conventional process in which the hybridization and the extension reaction were proceeded in separate liquid phases, such as carrying out the individual processes of hybridization, washing, addition of enzyme and monomers and extension, this embodiment allows the hybridization and the extension reaction to proceed in a single liquid phase, that is, allows use of the reaction system remained unexchanged.

In step S170, the cDNA chain 18 and the DNA primer for extension contained in the MPEC sample form a double strand by the above-described annealing, then in step S180, a DNA chain 19 extends complementarily to the cDNA chain 18 with the aid of an enzyme system for DNA chain extension, which is typically Klenow fragment, to thereby synthesize a double-stand (ds)DNA 21 (FIG. 6D, FIG. 7D). By allowing the MPEC sample to be introduced in step S150 to preliminarily contain the above-described labeled nucleic acid besides the nucleotide monomers (dNTP), the DNA chain 19 may be labeled, and thereby also the dsDNA chain 21 formed on the carrier 12 may be labeled.

In step S190, similarly to as in step S40 in FIG. 2, the reaction solution is discarded, and the carrier 12 is washed typically using a 0.1 wt % SDS solution.

In step S200, the dsDNA 21 shown in FIG. 6D and FIG. 7D is detected. More specifically, fluorometric detection using labeled nucleotide monomers, such as Cy™ 3-dUTP, introduced in step S150, or fluorometric detection based on fluorescent dyeing with the aid of BCIP/NBT reaction using nucleotide monomers introduced with biotin, or a chromogenic method applied to ELISA, may be carried out. Portions corresponded to the reaction spaces 20 having the dsDNA 21 formed therein, as shown in FIG. 7E, are visualized, indicating that the dsDNA 21 was formed in thus visualized reaction spaces.

Similarly to as in the first embodiment, as shown in FIG. 7E, if a plurality of reaction spaces 20 are provided independently from each other to form an array on the carrier 12, screening may be accessible by varying, for every reaction space 20, reaction conditions, such as types of primer, concentration of the reagents, types of enzyme for DNA chain extension and so forth.

THIRD EMBODIMENT

Figure 8:
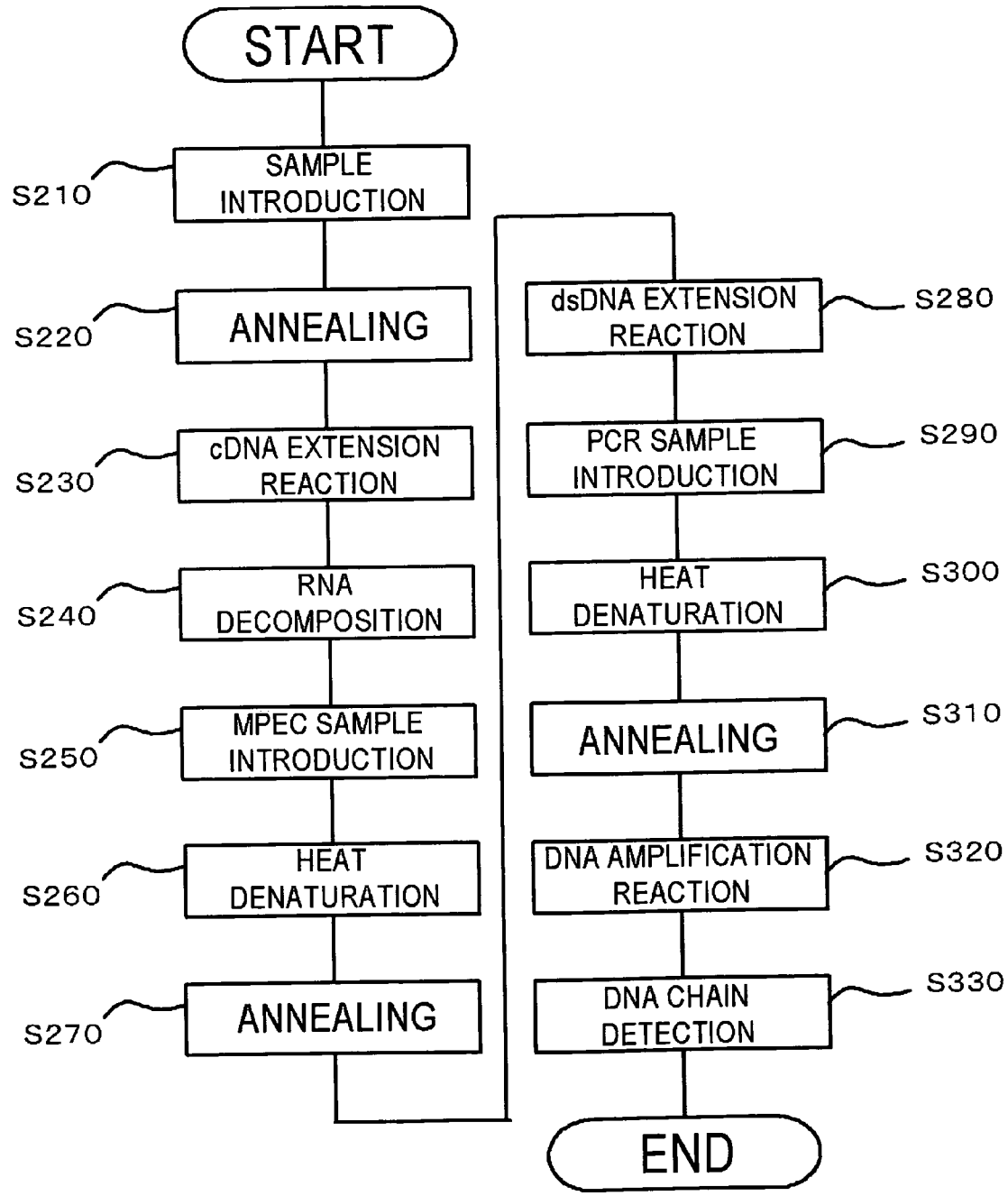
FIG. 8 A flow chart showing an RNA detection method according to a third embodiment.

FIG. 8 is a flow chart showing procedures of the RNA detection method as a third embodiment. FIG. 9A to FIG. 9D and FIG. 10A to FIG. 10E are drawings schematically showing the reactions proceeded in the reaction space of the carrier, according to the flow chart shown in FIG. 8.

The RNA detection method includes a first step introducing, into the reaction space 20 provided on the carrier 12, a sample 22 containing the target sample, which is typically cell lysate of target cells, an enzyme system for DNA chain extension and nucleotide monomers (step S210), and allowing a DNA chain extension reaction to proceed ahead of the immobilized DNA primer (primer 14), while using an RNA chain 16 contained in the target sample as a template, to thereby form a cDNA chain (steps S220, S230); a second step decomposing the RNA chain 16 in the reaction system containing the above-described cell lysate of the target cells, after the DNA chain extension reaction (step S240); a third step introducing, into the reaction system containing the cDNA chain 18, a mixture containing a DNA primer for extension, an enzyme system for DNA chain extension and nucleotide monomers (step S250), and synthesizing a double-strand DNA 21, while using the cDNA chain 18 as a template (steps S260, S270, S280); a fourth step synthesizing the double-strand (ds)DNAs 21, while respectively using the single-strand DNAs obtained by heat denaturation (step S300) of the double-strand DNA 21 as templates, to thereby amplify the double-strand DNA 21 (steps S310, S320); and a fifth step detecting the amplified double-strand DNAs 21.

Figure 9:
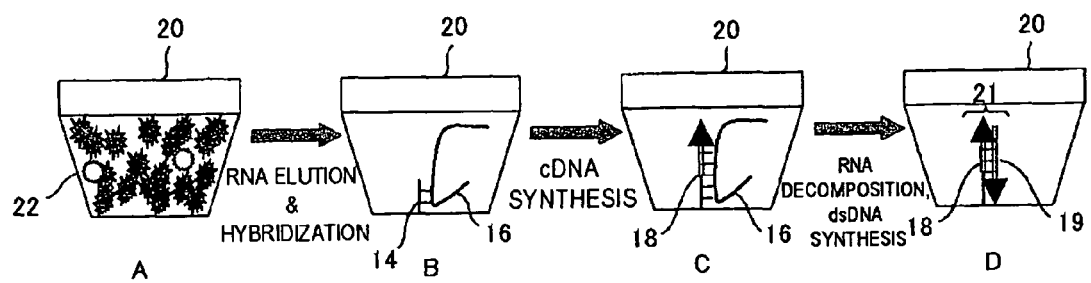
FIG. 9 A drawing schematically showing a reaction takes place in the reaction space of the substrate according to the flow chart shown in FIG. 8.
Figure 10:
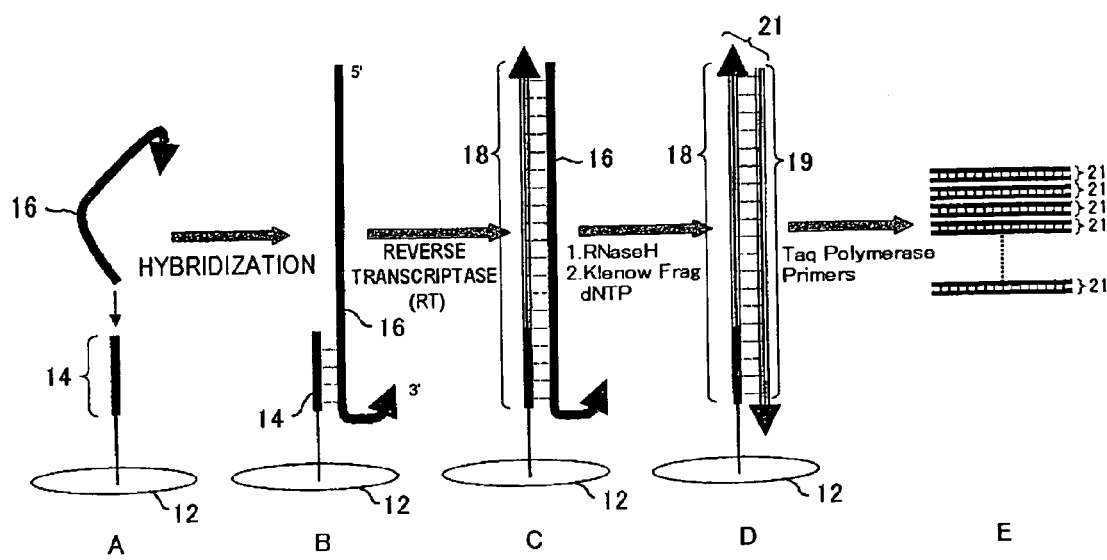
FIG. 10 A drawing schematically showing a reaction takes place in the reaction space of the substrate according to the flow chart shown in FIG. 8.

According to FIG. 8, in step S210, similarly to as in step S10 in FIG. 2, the sample is introduced into the reaction space 20 having the primer 14 immobilized therein (FIG. 9A, FIG. 10A). It has been described that, in FIG. 2, at least one species of nucleotide monomers in the sample introduced into the reaction space 20 may be labeled, whereas in this embodiment, a label is not introduced in the step of extending cDNA chain described later.

In step S220, similarly to as in step S20 in FIG. 2, RNA is eluted, if necessary, from the sample 22 and annealed, so as to hybridize the primer 14 having a sequence complementary to a part of the template RNA chain 16 with such RNA chain 16, to thereby form a double strand (FIG. 9B, FIG. 10B). It is to be noted that, similarly to as in the first embodiment, any primer 14 having no sequence complementary to any portions of the sequence of the RNA chain 16 never forms the double strand.

In step S230, similarly to as in step S30 in FIG. 2, reverse transcription reaction proceeds at the 3'-terminal of the primer 14, while using the RNA chain 16 as a template, under the action of the enzyme system for DNA chain extension, thereby extension reaction of the DNA chain proceeds, and the cDNA chain 18 complementary to the RNA chain 16 is formed on the carrier 12 (FIG. 9C, FIG. 10C).

In step S240, ribonuclease H, specifically decomposing RNA chain contained in RNA-DNA hybrid, is introduced into the reaction system, to thereby decompose only the RNA chain 16.

In step S250, an MPEC sample containing a DNA primer for extension (not shown) having a sequence complementary to a part of the cDNA chain 18 as a template DNA chain, an enzyme system for DNA chain extension, and nucleotide monomers (dNTP) is introduced. Klenow fragment, for example, may be exemplified as the enzyme system for DNA chain extension. Unlike the second embodiment, the nucleotide monomers used herein will not be introduced with a label, because the DNA amplification reaction follows.

In step S260, temperature of the reaction system introduced with the sample is elevated to not less than a temperature of heat denaturation (melting temperature: Tm) of DNA chain, typically up to 90° C. to 95° C. By the heat denaturation, the cDNA chain and DNA primer for extension, formed on the carrier, having folded structures such as those observed in self-complementary chain, are converted to straight single strand. The reaction system is directly brought into step S270, without washing, similarly to as in the second embodiment.

In step S270, annealing such as described in the above is carried out, thereby the cDNA chain 18, and the DNA primer for extension contained in the MPEC sample form a double strand, the process advances to step S280, wherein extension reaction of the DNA chain 19 complementary to the cDNA chain 18 proceeds under the action of the enzyme system for DNA chain extension, such as Klenow fragment, thereby the double-strand (ds)DNA 21 is synthesized (FIG. 9D, FIG. 10D).

In step S290, a PCR sample containing the individual primers having sequences respectively complementary to a part of each of the cDNA chain 18 and the DNA chain 19, as template DNA chains, an enzyme system for DNA chain extension, and nucleotide monomers is introduced. Taq polymerase, representatively used in PCR, may be exemplified as the enzyme system for DNA chain extension.

In step S300, temperature of the reaction system introduced with the sample is elevated to not less than a temperature of heat denaturation (melting temperature: Tm) of DNA chain, typically up to 90° C. to 95° C. The reaction system is directly brought into step S310, without washing, similarly to as in step S260.

In step S310, annealing such as described in the above is carried out, thereby the cDNA chain 18 or the DNA chain 19, and the primers respectively corresponded to the both, contained in the PCR sample form a double strand, the process advances to step S320, wherein the DNA amplification reaction proceeds under the action of the enzyme system for DNA chain extension, thereby the double-strand (ds)DNA 21 is amplified (FIG. 10E).

In step S330, as shown in FIG. 10E, the dsDNA 21 amplified in step S320 is detected. More specifically, it may be detected in a fluorometric manner, using a reagent capable of selectively detecting the double-strand DNA, such as SYBR® Green.

Similarly to as in the first embodiment, if a plurality of reaction spaces 20 are provided independently from each other to form an array on the carrier 12, screening may be accessible by varying, for every reaction space 20, reaction conditions, such as types of primer, concentration of the reagents, types of enzyme for DNA chain extension and so forth.

FOURTH EMBODIMENT

Figure 11:
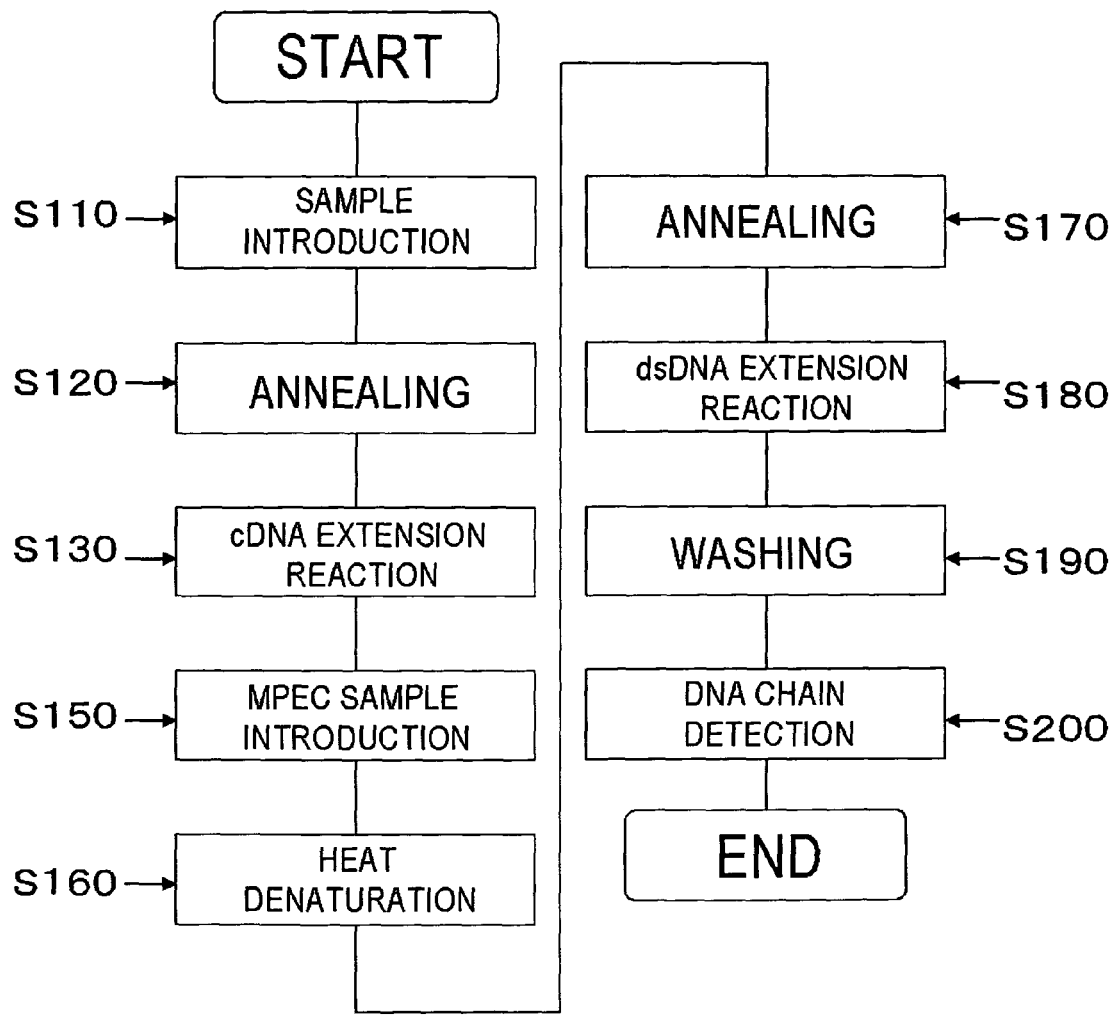
FIG. 11 A flow chart showing an RNA detection method according to a fourth embodiment.

FIG. 11 is a flow chart showing procedures of the RNA detection method as a fourth embodiment. FIG. 12A to FIG. 12D and FIG. 13A to FIG. 13E are drawings schematically showing the reactions proceeded in the reaction space of the carrier, according to the flow chart shown in FIG. 11.

The RNA detection method includes a first step introducing, into the reaction space 20 provided on the carrier 12, a sample 22 containing the target sample, which is typically cell lysate of target cells, an enzyme system for DNA chain extension and nucleotide monomers (step S110), and allowing a DNA chain extension reaction to proceed ahead of the immobilized DNA primer (primer 14), while using an RNA chain 16 contained in the target sample as a template, to thereby form a cDNA chain 18 (steps S120, S130); a second step introducing, into the reaction system containing the cDNA chain 18, a mixture containing a DNA primer for extension, an enzyme system for DNA chain extension and nucleotide monomers (step S150), and synthesizing a double-strand (ds) DNA 21, while using the cDNA chain 18 as a template (steps S160, S170, S180); and a third step detecting the synthesized double-strand DNA 21 (step S200).

This embodiment is similar to the second embodiment, except that step S140, which is a process of decomposing the RNA chain 16 hybridized with the cDNA chain 18 in the second embodiment (FIG. 6C, FIG. 7C), is not carried out.

Figure 12:
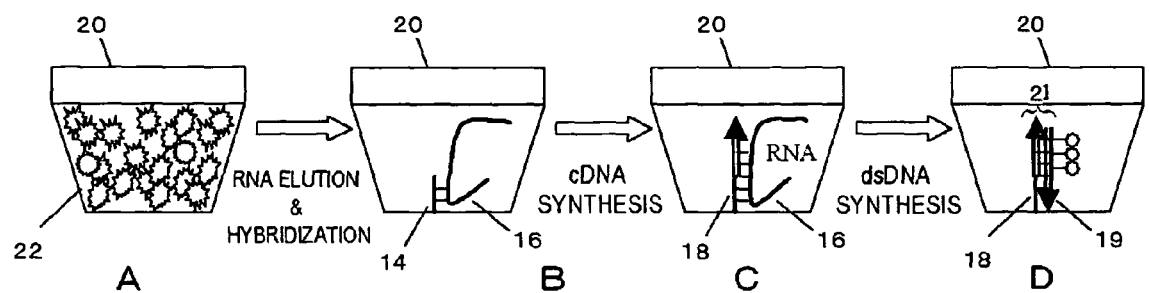
FIG. 12 A drawing schematically showing a reaction takes place in the reaction space of the substrate according to the flow chart shown in FIG. 11.
Figure 13:
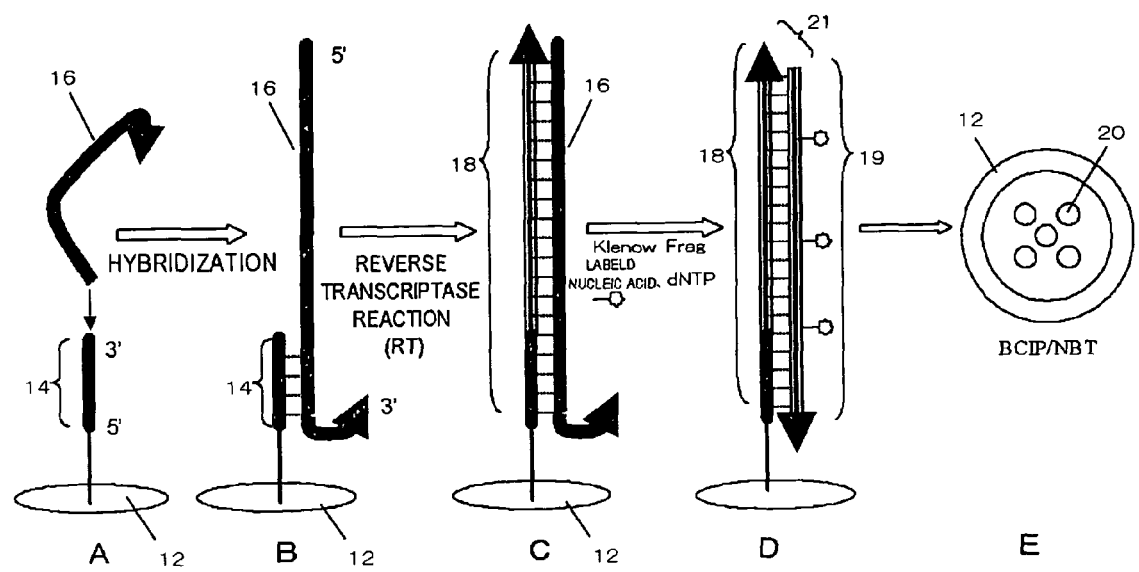
FIG. 13 A drawing schematically showing a reaction takes place in the reaction space of the substrate according to the flow chart shown in FIG. 11.

That is, according to FIG. 11, in step S110, similarly to as in step S10 in FIG. 2, the sample 22 is introduced into the reaction space 20 having the primer 14 immobilized therein (FIG. 12A, FIG. 13A). In step S120, similarly to as in step S20 in FIG. 2, RNA is eluted, if necessary, from the sample 22 and annealed, so as to hybridize the primer 14 having a sequence complementary to a part of the template RNA chain 16 with such RNA chain 16, to thereby form a double strand (FIG. 12B, FIG. 13B). In step S130, similarly to as in step S30 in FIG. 2, reverse transcription (RT) reaction takes place at the 3'-terminal of the primer 14, while using the RNA chain 16 as a template, under the action of the enzyme system for DNA chain extension, thereby extension reaction of the DNA chain proceeds, and the cDNA chain 18 complementary to the RNA chain 16 is formed on the carrier 12 (FIG. 12C, FIG. 13C). In step S150, an MPEC sample containing a DNA primer for extension (not shown) having a sequence complementary to a part of the cDNA chain 18 as a template DNA chain, an enzyme system for DNA chain extension, and nucleotide monomers (dNTP) is introduced. Klenow fragment, for example, may be exemplified as the enzyme system for DNA chain extension. To the nucleotide monomers, at least one species of which may be introduced with a label, just like the nucleotide monomers introduced in step S10 in FIG. 2. In step S160, temperature of the reaction system introduced with the sample is elevated to not less than a temperature of heat denaturation (melting temperature: Tm) of DNA chain, typically up to 90° C. to 95° C. By the heat denaturation, the cDNA chain and DNA primer for extension, formed on the carrier, having folded structures such as those observed in self-complementary chain, are converted to straight single strand. The reaction system is directly brought into step S170, without washing. In step S170, annealing such as described in the above is carried out, thereby the cDNA chain 18, and the DNA primer for extension contained in the MPEC sample form a double strand, the process advances to step S180, wherein extension reaction of the DNA chain 19 complementary to the cDNA chain 18 proceeds under the action of the enzyme system for DNA chain extension, such as Klenow fragment, thereby the double-strand (ds)DNA 21 is synthesized (FIG. 6D, FIG. 7D). By allowing the MPEC sample to be introduced in step S150 to preliminarily contain the above-described labeled nucleic acid besides the nucleotide monomers (dNTP), the DNA chain 19 may be labeled, and thereby also the dsDNA chain 21 formed on the carrier 12 may be labeled. In step S190, similarly to as in step S40 in FIG. 2, the reaction solution is discarded, and the carrier 12 is washed typically using a 0.1 wt % SDS solution. In step S200, the dsDNA 21 shown in FIG. 12D and FIG. 13D is detected.

More specifically, the dsDNA chain 21 is detected, by using a technique using a BCIP/NBT reagent as described in the above, so as to visualize a portion corresponded to the reaction space 20 having the dsDNA 21 formed therein on the carrier 12 (FIG. 13E).

FIFTH EMBODIMENT

Figure 14:
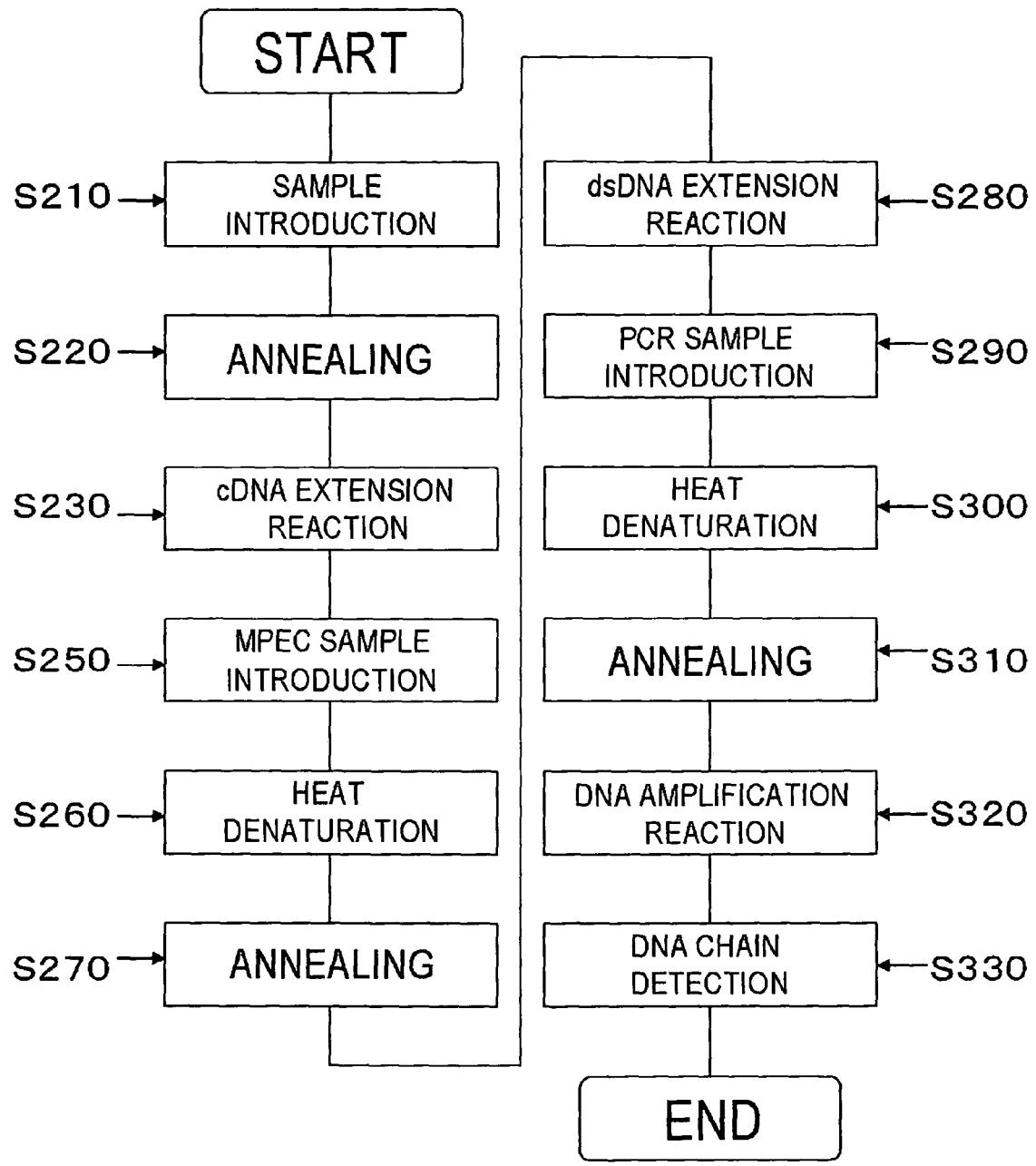
FIG. 14 A flow chart showing an RNA detection method according to a fifth embodiment.

FIG. 14 is a flow chart showing procedures of the RNA detection method as a fifth embodiment. FIG. 15A to FIG. 15D and FIG. 16A to FIG. 16E are drawings schematically showing the reactions proceeded in the reaction space of the carrier, according to the flow chart shown in FIG. 14.

The RNA detection method includes a first step introducing, into the reaction space 20 provided on the carrier 12, a sample 22 containing the target sample, typically cell lysate of target cells, an enzyme system for DNA chain extension and nucleotide monomers (step S210), and allowing a DNA chain extension reaction to proceed ahead of the immobilized DNA primer (primer 14), while using an RNA chain 16 contained in the target sample as a template, to thereby form a cDNA chain (steps S220, S230); a second step introducing, into the reaction system containing the cDNA chain 18, a mixture containing a DNA primer for extension, an enzyme system for DNA chain extension and nucleotide monomers (step S250), and synthesizing the double-strand (ds) DNA 21, while using the cDNA chain 18 as a template (steps S260, S270, S280); a third step synthesizing double-strand DNAs 21, while respectively using the individual single-strand DNAs obtained by heat denaturation (step S300) of the double-strand DNA 21 as templates, to thereby amplify the double-strand DNA 21 (steps S310, S320); and a fourth step detecting the amplified double-strand DNAs 21 (step S330).

This embodiment is similar to the second embodiment, except that step S140, which is a process of decomposing the RNA chain 16 hybridized with the cDNA chain 18 in the third embodiment (FIG. 9C, FIG. 10C), is not carried out.

Figure 15:
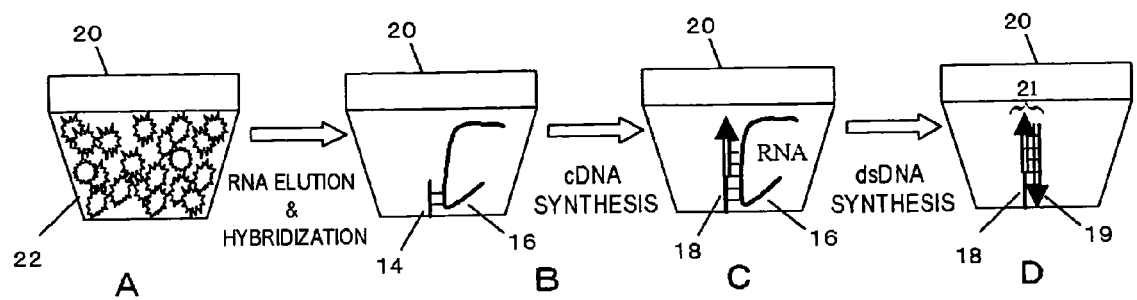
FIG. 15 A drawing schematically showing a reaction takes place in the reaction space of the substrate according to the flow chart shown in FIG. 14.
Figure 16:
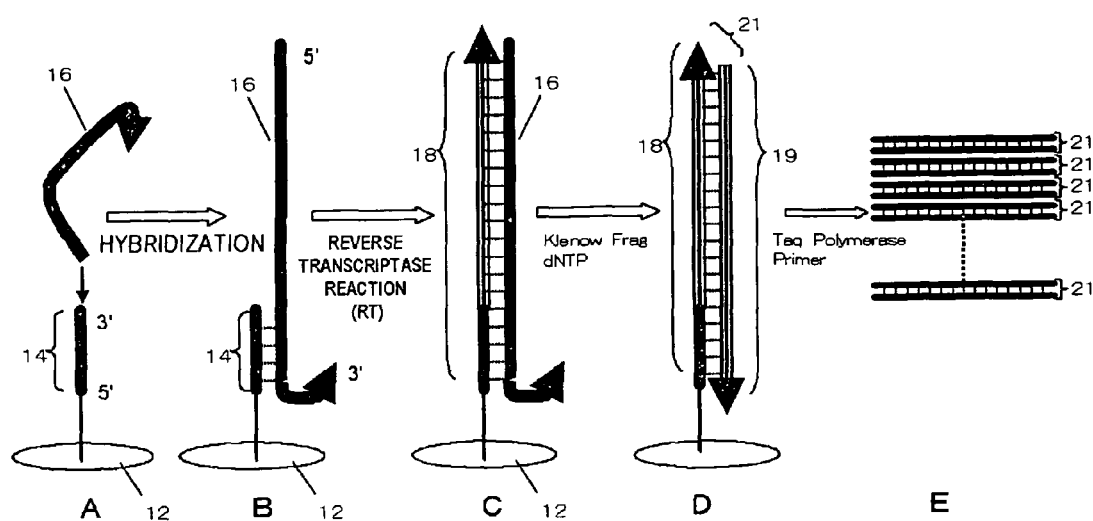
FIG. 16 A drawing schematically showing a reaction takes place in the reaction space of the substrate according to the flow chart shown in FIG. 14.

According to FIG. 14, in step S210, similarly to as in step S10 in FIG. 2, the sample 22 is introduced into the reaction space 20 having the primer 14 immobilized therein (FIG. 15A, FIG. 16A). In step S220, similarly to as in step S20 in FIG. 2, RNA is eluted, if necessary, from the sample 22 and annealed, so as to hybridize the primer 14 having a sequence complementary to a part of the template RNA chain 16 with such RNA chain 16, to thereby form a double strand (FIG. 15B, FIG. 16B). In step S230, similarly to as in step S30 in FIG. 2, reverse transcription (RT) reaction takes place at the 3'-terminal of the primer 14, while using the RNA chain 16 as a template, under the action of the enzyme system for DNA chain extension, thereby extension reaction of the DNA chain proceeds, and the cDNA chain 18 complementary to the RNA chain 16 is formed on the carrier 12 (FIG. 15C, FIG. 16C). In step S250, an MPEC sample containing a DNA primer for extension (not shown) having a sequence complementary to a part of the cDNA chain 18 as a template DNA chain, an enzyme system for DNA chain extension, and nucleotide monomers (dNTP) is introduced. Klenow fragment, for example, may be exemplified as the enzyme system for DNA chain extension. In step S260, temperature of the reaction system introduced with the sample is elevated to not less than a temperature of heat denaturation (melting temperature: Tm) of DNA chain, typically up to 90° C. to 95° C. By the heat denaturation, the cDNA chain and DNA primer for extension, formed on the carrier, having folded structures such as those observed in self-complementary chain, are converted to straight single strand. The reaction system is directly brought into step S270, without washing. In step S270, annealing such as described in the above is carried out, thereby the cDNA chain 18, and the DNA primer for extension contained in the MPEC sample form a double strand, the process advances to step S280, wherein extension reaction of the DNA chain 19 complementary to the cDNA chain 18 proceeds under the action of the enzyme system for DNA chain extension, thereby the double-strand (ds)DNA 21 is synthesized (FIG. 15D, FIG. 16D). In step S290, a PCR sample containing the individual primers having sequences respectively complementary to a part of each of the cDNA chain 18 and the DNA chain 19, as template DNA chains, an enzyme system for DNA chain extension, and nucleotide monomers is introduced. Taq polymerase, representatively used in PCR, may be exemplified as the enzyme system for DNA chain extension. In step S300, temperature of the reaction system introduced with the sample is elevated to not less than a temperature of heat denaturation (melting temperature: Tm) of DNA chain, typically up to 90° C. to 95° C. The reaction system is directly brought into step S310, without washing, similarly to the case of step S260. In step S310, annealing such as described in the above is carried out, thereby the cDNA chain 18 or the DNA chain 19, and the primers respectively corresponded to the both, contained in the PCR sample form a double strand, the process advances to step S320, wherein the DNA amplification reaction proceeds under the action of the enzyme system for DNA chain extension, thereby the double-strand (ds)DNA 21 is amplified (FIG. 16E). In step S330, as shown in FIG. 16E, the dsDNA 21 amplified in step S320 is detected. More specifically, it may be detected in a fluorometric manner, using a reagent capable of selectively detecting the double-strand DNA, such as SYBR® Green.

SIXTH EMBODIMENT

Figure 17:
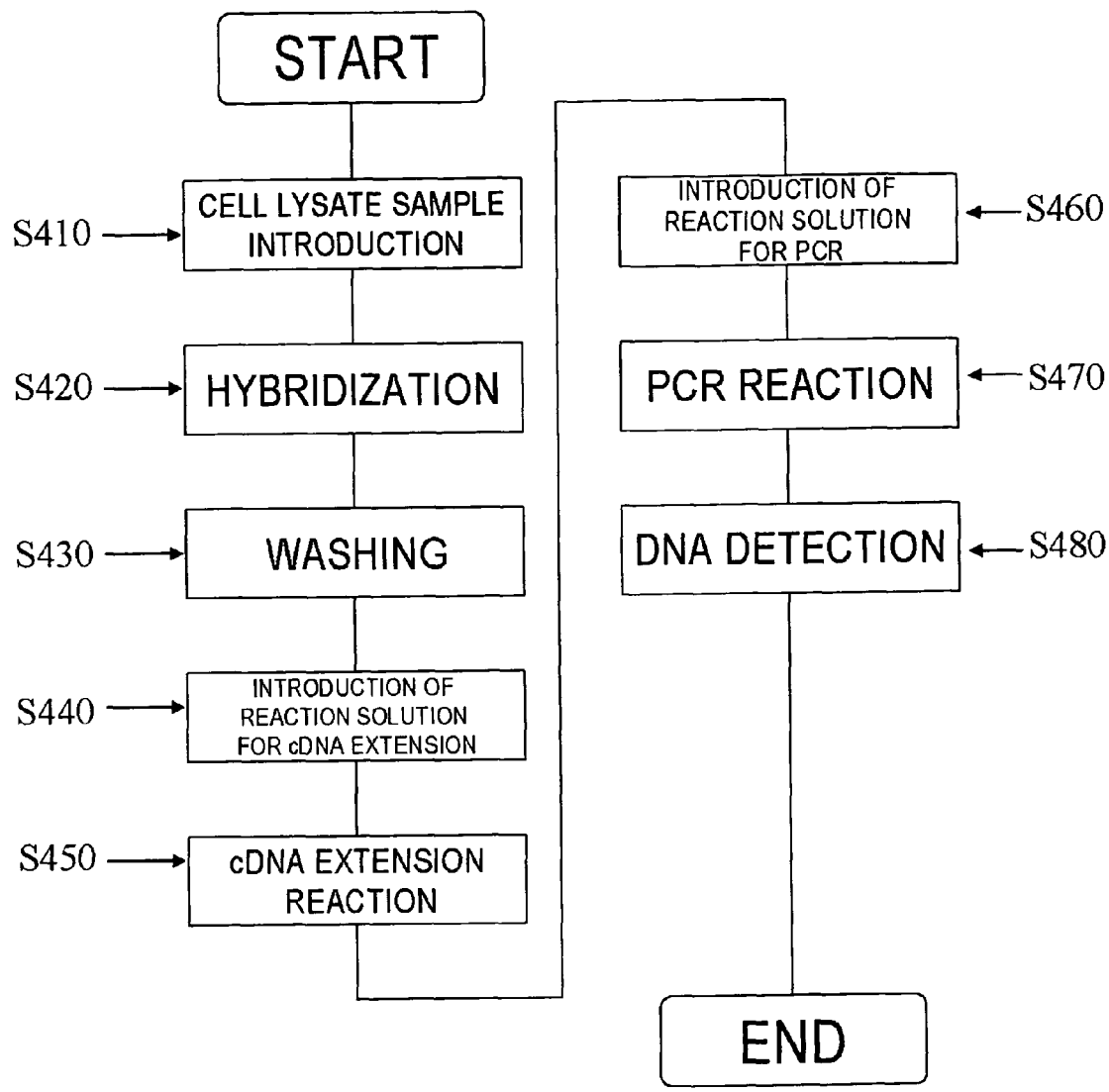
FIG. 17 A flow chart showing an RNA detection method according to a sixth embodiment.

FIG. 17 is a flow chart showing procedures of the RNA detection method as a sixth embodiment. FIG. 18A to FIG. 18D and FIG. 19A to FIG. 19D are drawings schematically showing the reactions proceeded in the reaction space of the substrate, according to the flow chart shown in FIG. 17.

The RNA detection method is characterized as a reverse transcription-polymerase chain reaction (RT-PCR) method, and includes the individual steps of transferring a target sample, which is typically cell lysate of target cells, into a reaction space having the above-described surface (step S410), hybridizing a mRNA in the target sample with an immobilized nucleic acid primer (step S420); allowing RT-PCR to proceed in the reaction space using an appropriate buffer solution (steps S450, S470); and detecting a desired PCR product (step S480).

That is, the method includes a first step introducing a sample 22, typically containing cell lysate, into the reaction space 20 provided on the carrier 12 (step S410), and allowing hybridization to proceed (step S420), a second step for washing (step S430), a third step introducing a sample 23 containing an enzyme system for DNA chain extension and nucleotide monomers (step S440), and allowing a DNA chain extension reaction of the immobilized DNA primer (primer 14) to proceed, while using the RNA chain 16 contained in the cell lysate as a template, to thereby form a cDNA chain (step S450), a fourth step introducing, into the reaction system containing the cDNA chain 18, a sample 24 containing a DNA primer for extension, an enzyme system for DNA chain extension and nucleotide monomers (step S460), allowing a PCR reaction to proceed while using the cDNA chain 18 as a template, to thereby amplify the double-strand DNA 21 (step S470), and a fifth step detecting the amplified double-strand DNA 21 (step S480).

Figure 18:
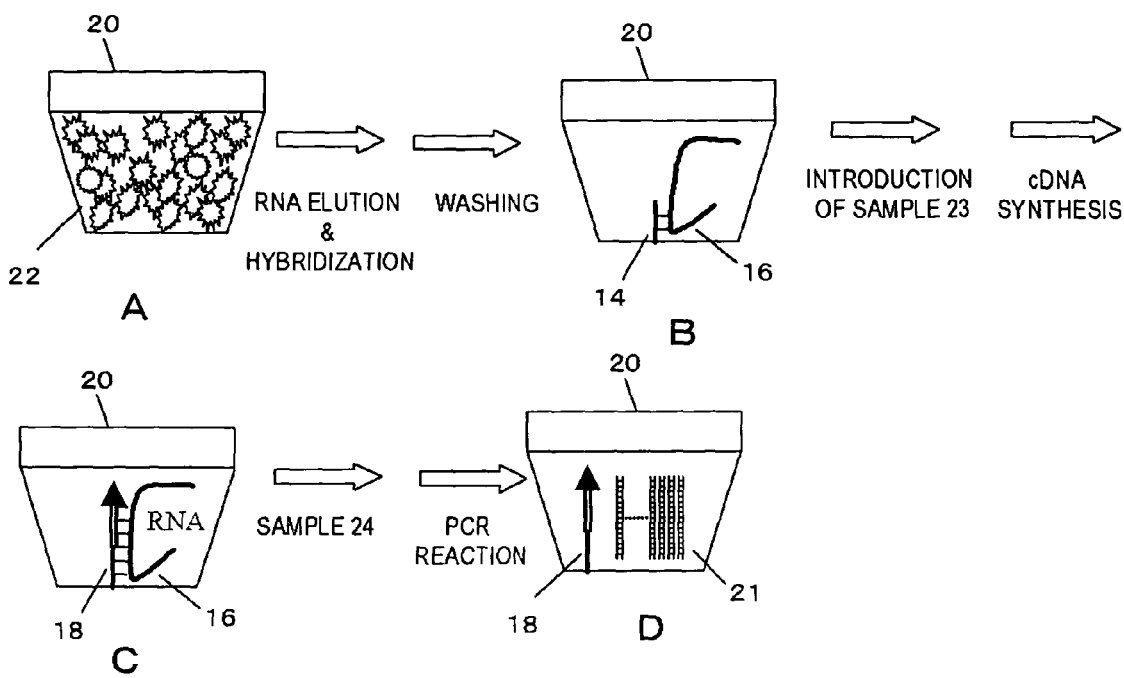
FIG. 18 A drawing schematically showing a reaction takes place in the reaction space of the substrate according to the flow chart shown in FIG. 17.
Figure 19:
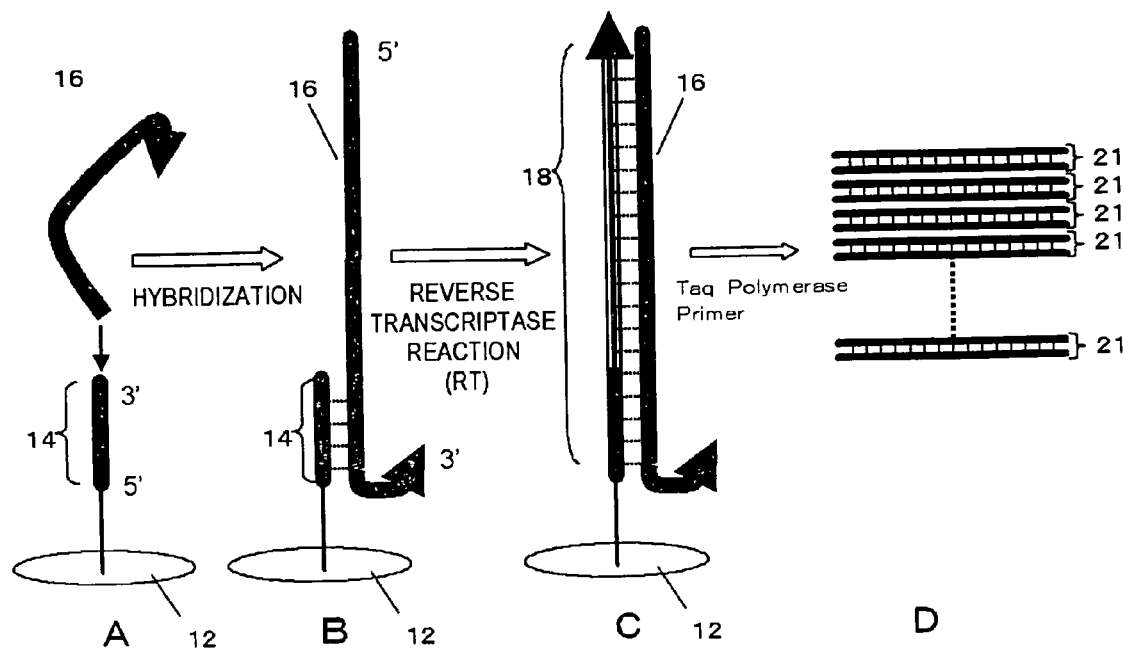
FIG. 19 A drawing schematically showing a reaction takes place in the reaction space of the substrate according to the flow chart shown in FIG. 17.

According to FIG. 17, in step S410, a sample 22 containing the cell lysate is introduced into the reaction space 20 having the primer 14 immobilized therein (FIG. 18A, FIG. 19A). The solution containing the cell lysate herein may be prepared as containing a reagent for inhibiting or inactivating RNase activity, which is typically DEPC (Diethylprocarbonate), and also by using a buffer solution for adjusting pH and salt concentration for hybridization. So far as the enzyme reaction by the enzyme system for DNA chain extension in step S450, and also in step S470 if necessary, will not be inhibited, or designed to reduce such inhibition against the enzyme reaction as described in the above, the sample 22 containing the cell lysate to be introduced in step S410 may be added with enzyme system for DNA chain extension and the oligo nucleotide monomers contained in the sample 23 and the sample 24 which are to be introduced as in step S440, and also in step S460 if necessary, and the washing in step S40 (step S430) and the introduction of the reaction solution for cDNA extension (step S440) may be omissible. Incidentally, the target sample such as cell lysate may contain guanidine or protease or phenol.

In step S420, RNA is eluted, if necessary, from the sample 22, and hybridization is allowed to proceed, to thereby form a double strand between the primer 14 having a sequence complementary to a part of the template RNA chain 16, and such RNA chain 16. Any primer 14 having no sequence complementary to any portions of the sequence of the RNA chain 16 never forms the double strand. By using an oligo dT primer as the primer 14, poly-A owned by mRNA may be captured. The target RNA chain is not limited to mRNA, and use of a DNA primer having a sequence specific to the primer 14 allows capture of RNA chain and DNA chain specific thereto.

In step S430, by washing the reaction space 20, the sample 22 in the reaction space may be removed while leaving the double strand formed between the primer 14 and the RNA chain 16 (FIG. 18B, FIG. 19B). Because the surface coated with the above-described polymer shows, by contribution of the hydrophilic group thereof, an effect of preventing non-specific adsorption of biological molecules contained in the target sample, such as cell lysate, the RNA chains other than the hybridized RNA chain 16 may be removed by washing, allowing purification of pure mRNA. If a plastic surface, such as polystyrene or polypropylene, having no polymer substance described in the above on the surface thereof, is used, any inhibitory substances against the enzyme reaction in the later processes cannot be removed, and this may adversely affect the detection.

In step S440, the reaction solution for cDNA extension (sample 23) is introduced into the reaction space 20 having the RNA chain 16 captured therein by the primer 14. In this reaction solution for cDNA extension, the above-described enzyme system for DNA chain extension, and nucleotide monomers are contained. For the case where a reaction solution containing a reverse transcriptase and a DNA polymerase, or a reaction solution containing rTth polymerase as the enzyme system for DNA chain extension, the PCR reaction in step S470 may be proceeded without exchanging the buffer solution in the reaction space, so that step S460 may be omissible.

In step S450, reverse transcription (RT) reaction takes place at the 3'-terminal of the primer 14, while using the RNA chain 16 as a template, under the action of the enzyme system for DNA chain extension, thereby extension reaction of the DNA chain proceeds, and the cDNA chain 18 complementary to the RNA chain 16 is formed on the carrier 12 (FIG. 18C, FIG. 19C). Incidentally, after the cDNA chain 18 was obtained, the DNA amplification reaction based on the PCR method in step S470 may be proceeded, without removing the RNA chain 16 which is a mRNA hybridized with the immobilized nucleic acid primer 14.

In step S460, a PCR reaction solution (sample 24) containing a primer having a sequence complementary to a part of the cDNA chain 18, as a template DNA chain, an enzyme system for DNA chain extension, and nucleotide monomers is introduced. A heat-resistant enzyme, such as Taq polymerase representatively used in PCR, may be exemplified as the enzyme system for DNA chain extension. If quantification using a fluorescent dye based on a quantitative PCR reaction is carried out in step S480, the reaction solution is necessarily introduced with a fluorescent probe such as TaqMan probe, or a fluorescent molecule such as SYBR® Green. Incidentally, if detection based on hybridization using a DNA micro-array is carried out, at least one species of the nucleotide monomers is necessarily labeled.

In step S470, a DNA amplification reaction (PCR) takes place based on interactions among the cDNA chain 18, the primer having a sequence complementary to a part of the cDNA chain 18 and the enzyme system for DNA chain extension, thereby the double-strand (ds) DNA 21 is amplified (FIG. 18D, FIG. 19D).

In step S480, the dsDNA chain 21 shown in FIG. 18D and FIG. 19D is detected. More specifically, a technique similar to that for detecting the dsDNA chain in step S200 in FIG. 5 may be adoptable.

As has been described in the above, step S460 may be omissible, when a single-step-type, RT-PCR reaction solution, in which a reaction ascribable typically to a reverse transcriptase for synthesizing cDNA, and a reaction ascribable typically to a DNA polymerase for PCR reaction may be proceeded in a single reaction solution, is used in step S440 to step S470.

The cDNA chain 18 formed in step S450 stably resides in a form of DNA chain on the surface of the carrier 12, and may therefore be stored as a solid-phase cDNA in the reaction space 20.

The method may further include, after the detection of the dsDNA chain 21 as the target PCR product in step S480, a step of washing the reaction space so as to leave the synthesized cDNA chain 18 immobilized therein, allowing PCR to proceed by using the primer same as that used in the above-described step of RT-PCR, or appropriate one different therefrom, and measuring the desired PCR product. It may still also be allowable to repeat the step of washing, the step of allowing PCR to proceed, and the step of measurement.

The reaction space 20 may be given in a form of PCR tube or PCR microplate, and thereby an RNA detection method useful for screening technique may be provided.

SEVENTH EMBODIMENT

Figure 20:
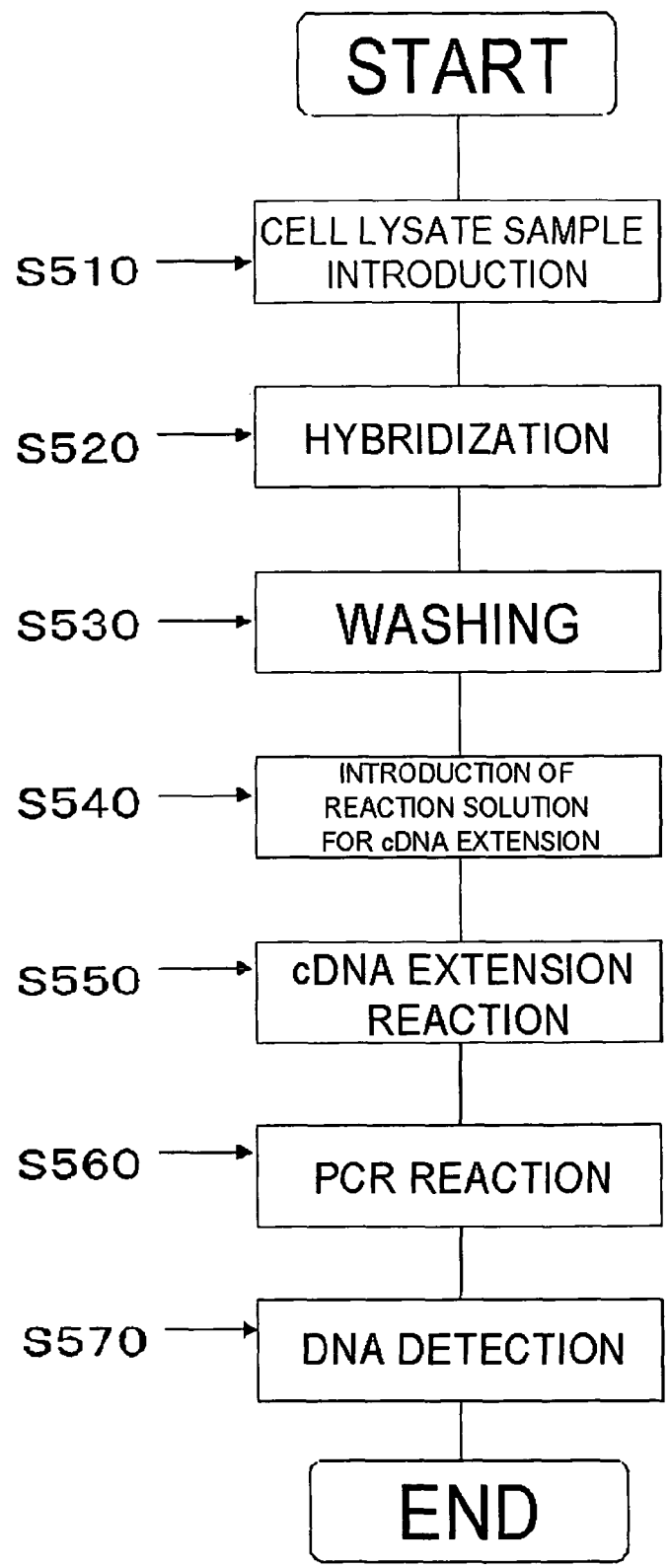
FIG. 20 A flow chart showing an RNA detection method according to a seventh embodiment.
Figure 21:
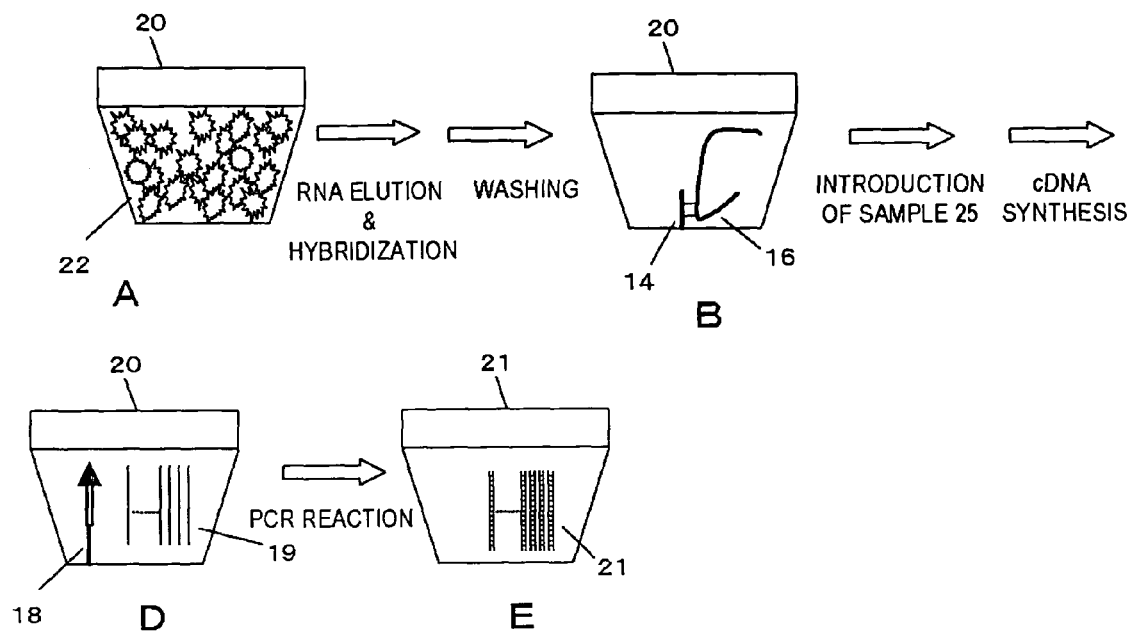
FIG. 21 A drawing schematically showing a reaction takes place in the reaction space of the substrate according to the flow chart shown in FIG. 20.

FIG. 20 is a flow chart showing procedures of the RNA detection method as a seventh embodiment. FIGS. 21A, B, D, E and FIG. 22A to FIG. 22C are drawings schematically showing the reactions proceeded in the reaction space of the substrate, according to the flow chart shown in FIG. 20.

The RNA detection method includes the individual steps of transferring the target sample, which is typically cell lysate of target cells, into the reaction space having the surface described in the above (step S510); hybridizing a mRNA in the target sample with the immobilized nucleic acid primer (step S520); introducing a reaction solution for reverse transcription, containing a primer for DNA chain extension, into the liquid phase (step S540); and producing a liquid-phase cDNA by reverse transcription (step S560).

That is, the method includes a first step introducing a sample 22, typically containing cell lysate, into the reaction space 20 provided on the carrier 12 (step S510), and allowing hybridization to proceed (step S520), a second step for washing (step S530), a third step introducing a sample 25 containing an enzyme system for DNA chain extension and nucleotide monomers (step S540), and allowing a DNA chain extension reaction ahead of the DNA primer (primer 15) to proceed, while using the RNA chain 16 contained in the cell lysate as a template, to thereby form a cDNA chain 19 (step S550), a fourth step allowing a PCR reaction to proceed in a reaction system containing a primer for DNA extension of a part of the cDNA chain 19, an enzyme system for DNA chain extension and nucleotide monomers, to thereby amplify the double-strand DNA 21 (step S560), and a fifth step detecting the amplified double-strand DNA 21 (step S570).

Figure 22:
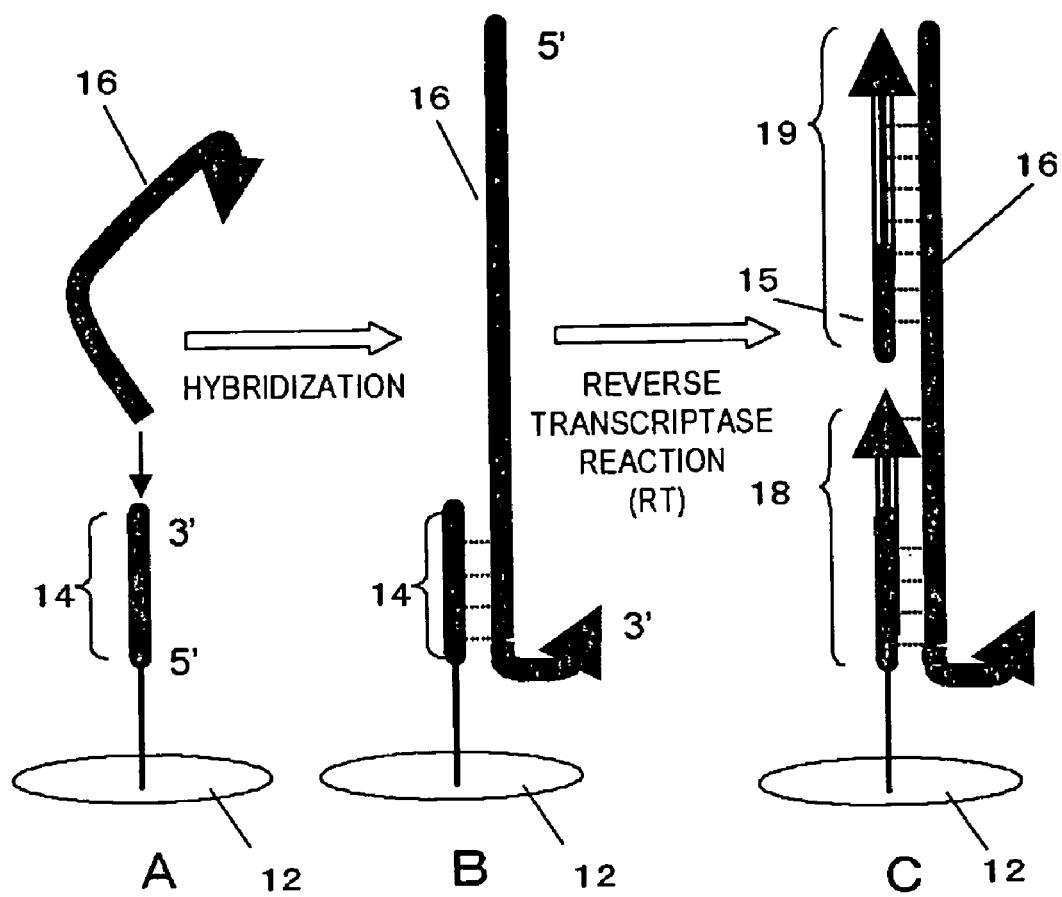
FIG. 22 A drawing schematically showing a reaction takes place in the reaction space of the substrate according to the flow chart shown in FIG. 20.

According to FIG. 20, in step S510, similarly to as in step S410 in FIG. 17, the sample 22 is introduced into the reaction space 20 having the primer 14 immobilized therein (FIG. 21A, FIG. 22A). The solution containing the cell lysate herein may be prepared as containing a reagent for inhibiting or inactivating RNase activity, and also by using a buffer solution for adjusting pH and salt concentration for hybridization. The target sample such as cell lysate may also contain guanidine or protease or phenol.

In step S520, similarly to as in step S420 in FIG. 17, RNA is eluted, if necessary, from the sample 22, and hybridization is allowed to proceed, to thereby form a double strand between the primer 14 having a sequence complementary to a part of the template RNA chain 16, and such RNA chain 16 (FIG. 6B, FIG. 7B). It is to be noted that, similarly to as in the first embodiment, any primer 14 having no sequence complementary to any portions of the sequence of the RNA chain 16 never forms the double strand. By using an oligo dT primer as the primer 14, poly-A owned by mRNA may be captured.

In step S530, similarly to as in step S430 in FIG. 17, by washing the reaction space 20, the sample 22 in the reaction space may be removed while leaving the double strand formed between the primer 14 and the RNA chain 16 (FIG. 21B, FIG. 22B).

In step S540, the reaction solution for cDNA extension (sample 25), containing an enzyme system for DNA chain extension and nucleotide monomers and a primer 15 for DNA chain extension, is introduced into the reaction space 20. An oligo DNA having a random sequence of 6 to 10 bases (referred to as "random primer", hereinafter) may generally be used as the primer for DNA chain extension. Incidentally, also a specific oligo DNA showing a specific complementarity with the RNA chain 16 may be adoptable. The nucleotide monomers contained in the sample 25 may be such as being labeled at least in one species thereof.

In step S550, reverse transcription (RT) reaction takes place at the 3'-terminals of the primer 14 and the primer 15 for DNA chain extension hybridized with the RNA chain 16 in the liquid phase, while using the RNA chain 16 as a template, under the action of the enzyme system for DNA chain extension, thereby extension reaction of the DNA chain proceeds, and the cDNA chain 18 complementary to the RNA chain 16 is formed on the carrier 12, and also the cDNA chain 19 complementary to the RNA chain 16 is formed in the liquid phase (FIG. 21D, FIG. 22C). When the random primer is used as the primer for DNA chain extension, the resultant cDNA chain 19 will not have a single length, because various portions of the primer may be in a complementary relation with the RNA chain 16. In step S540, if labeled nucleotide monomers are introduced, the cDNA chains 18, 19 may be labeled.

In step S560, a PCR reaction is allowed to proceed using a PCR reaction solution containing a primer (not shown), which is formed in step 550 while using a the cDNA chain 19 as a template DNA chain, and has a sequence complementary to a part of the cDNA chain 19, an enzyme system for DNA chain extension, and nucleotide monomers, thereby a DNA amplification reaction takes place, so as to amplify the double-strand (ds)DNA 21 (FIG. 22E). In step S570, the dsDNA chain 21 shown in FIG. 21E is detected. More specifically, a technique of detecting the dsDNA chain, similar to that used in step S200 in FIG. 5 may be used. The cDNA chain 19 formed in step 550 may be dividable since it resides in the liquid phase, so that the PCR reaction may be proceeded ahead of various primers. It may be storable in a frozen form, because it resides in a form of DNA chain. By using the cDNA chain 19 which resides in the liquid phase, it may be even possible to further amplify DNA or RNA. Method of the amplification herein may be exemplified by PCR method, LAMP method, NASBA method, TRC method and so forth.

The reaction space 20 may be given in a form of PCR tube or PCR microplate, and thereby an RNA detection method useful for screening technique may be provided.

According to this method, gene expression profile analysis, in particular, may be carried out only by simple operations using cell lysate as a sample, while getting rid of most of labor- and time-consuming sample preparation having been necessary in the general analyses.

EXAMPLES

Example 1

Fabrication of PMBN-Coated, 96-Well Microtiter Plate

A 96-well microtiter plate was molded by injection molding, using a saturated cyclic polyolefin resin. The individual wells were coated with PMBN, the bottom of the mold product was coated with PMBN, to thereby fabricate a PMBN-coated, 96-well microtiter plate according to an embodiment of the present invention. The plate will be referred to as "PMBN plate", hereinafter.

(Fabrication of 96-Well Microtiter Plate Introduced with Aldehyde Group)

A 96-well microtiter plate was molded by injection molding, using a saturated cyclic polyolefin resin. Thus-molded, 96-well titer plate was irradiated with oxygen plasma, introduced with amino group using aminosilane, and further introduced with aldehyde group using glutaraldehyde onto the amino group, to thereby fabricate a 96-well microtiter plate introduced with aldehyde group. The plate will be referred to as "aldehyde plate", hereinafter.

(Immobilization of Primer)

As the primer, each of an oligo DNA composed of a sequence specific to *E. coli* 23S ribosome RNA expressed as SEQ ID NO:1, an oligo DNA composed of a sequence specific to *Staphylococcus aureus* 23 S ribosome RNA expressed as SEQ ID NO:2, and an oligo DNA composed of a sequence specific to *Psudomonas aeruginosa* 23S ribosome RNA expressed as SEQ ID NO:3, all of which being shown in Table 1 below, as having the 5'-terminal modified with an amino group, was dissolved using a 0.25 M carbonate buffer (pH9.0), to respectively prepare 10 μM of oligo DNA solutions. Ten microliters each of the oligo DNA solutions were dispensed into the individual wells of the PMBN plate and the aldehyde plate, and the plates were then allowed to stand at 80° C. for 1 hour. After washing with ultra pure water, the individual wells were subjected to blocking.

The blocking herein means a process of inactivating, after immobilizing an oligo DNA to a substrate so as to give an immobilized primer, unreacted activated ester or aldehyde group portions which reside on the surface of the substrate, in order to prevent non-specific binding of DNA chain and RNA chain, and proteins and so forth of biological origin in the sample.

More specifically, as for the PMBN plate, each well was dispensed with 400 μl of an 1 mol/l NaOH solution as a blocking solution, allowed to stand for 5 minutes at room temperature, removed with the blocking solution, and washed with ultra pure water.

As for the aldehyde plate, a blocking solution was prepared by dissolving 0.6 g sodium borohydride and 50 ml of ethanol into 180 ml of phosphate buffer, each well was dispensed with 400 μl of the blocking solution, allowed to stand for 5 minutes at room temperature, removed with the blocking solution, and washed with ultra pure water.

After the blocking, 400 μl of a 1 wt % BSA-containing PBS(-) was spotted into each well, allowed to stand at room temperature for 2 hours, and washed three times by dispensing and sucking to remove 400 μl of a washing solution containing 0.05 wt % Tween® 20 (Polyoxyethylene Sorbitan Monolaurate) in PBS(-), and the plates were then dried.

TABLE 1

| Name of Primer | Sequence |
| --- | --- |
| E. COLI | SEQ ID NO: 1<br>5'-CGAGCAAGTCGCTTCACCTACATATCAG-3' |
| Staphylococcus aureus | SEQ ID NO: 2<br>5'-AATCGCACGCTTCGCCTATCCTACT-3' |
| Psudomonas aeruginosa | SEQ ID NO: 3<br>5'-AACCGACTAACCCTGCGTCGATTAAC-3' |

(Preparation of Total RNA Solution from *E. Coli*)

One hundred microliters of DEPC treated water, containing 1 μg of total RNA extracted from cultured *E. coli*, was kept at 65° C. for 5 minutes, and then quenched on ice. The RNA solution was added with a reaction solution prepared by adding reverse transcriptase M-MLV (Rnase H−), 5× reverse transcriptase M-MLV buffer, RNase inhibitor (super), 1 mM of biotin-labeled dUTP, 20 mM of DATP, 20 mM of dGTP, 20 mM of dCTP, and DEPC treated water. Fifty microliters each of this solution was dispensed into the individual wells, and incubated at 42° C. for 1 hour. After incubation, 200 μl of a TE buffer (10 mM Tris/HCl (pH8.5), 1 mM EDTA) was dispensed, the wells were washed twice with the TE buffer, then washed with ultra pure water, and dried.

Peroxidase-labeled avidin solution was dispensed, allowed to stand at room temperature for 30 minutes, the peroxidase-labeled avidin solution was removed, the wells were washed three times by dispensing and sucking to remove 400 μl of a washing solution containing 0.05 wt % Tween 20 in PBS(-), 100 μl each of a POD chromogenic substrate solution was dispensed into each well, allowed to stand under darkness for 15 minutes so as to proceed the chromogenic reaction, 100 μl each of a termination solution was dispensed into the individual wells, and state of development of color was measured based on absorbance using a plate reader.

Development of color of substrate indicates that the cDNA was synthesized while using RNA as a template, wherein higher absorbance indicates more efficient synthesis of cDNA.

Since the total RNA extracted from *E. coli* is used herein as a sample, specific detection of *E. coli* may be confirmed if only the wells having the oligo DNA, having a sequence specific to *E. coli* 23S ribosome RNA, immobilized therein as the primer develop color.

Intensities of fluorescence of the wells, having the oligo DNA chains corresponded to the individual sequences immobilized therein as the primers, on the PMBN plate and the aldehyde plate was shown in Table 2. Absorbance of the individual wells having the primers immobilized therein was determined, for each plate, by subtracting absorbance of the wells having no primers immobilized therein.

The reverse transcription on the PMBN plate was found to proceed only on the primer having the *E. coli*-specific sequence, proving excellent ability of the plate in specific RNA detection.

(Table 2)

TABLE 2

Absorbance

| Plate | Primer sequence | | |
|---|---|---|---|
| | *E. coli* | *Staphylococcus aureus* | *Psudomonas aeruginosa* |
| PMBN plate | 0.717 | 0.078 | 0.083 |
| Aldehyde plate | 0.264 | 0.185 | 0.157 |

Example 2

(Fabrication of PMBN-Coated Tube)

The inner surface of a PCR tube (MicroAmp® Strip Tubes, from Applied Biosystems) was coated with PMBN expressed by the general formula (2), to thereby fabricate a PMBN-coated tube according to one embodiment of the present invention. The tube will be referred to as "PMBN-coated tube", hereinafter.

(Fabrication of Aldehyde Group-Introduced Tube)

The inner surface of the (MicroAmp Strip Tubes, from Applied Biosystems) was irradiated with oxygen plasma, introduced with amino group using aminosilane, and further introduced with aldehyde group on the amino group using glutaraldehyde, to thereby fabricate an aldehyde group-introduced tube. The tube will be referred to as "aldehyde tube", hereinafter.

(Immobilization of Primer)

As the primer, an oligo DNA expressed as SEQ ID NO:4 shown in Table 3 below, having the 5'-terminal thereof modified with an amino group, was respectively dissolved using a 0.25 M carbonate buffer (pH9.0), to prepare 10 µM of oligo DNA solution. Ten microliters each of the oligo DNA solution was dispensed into the individual tubes of the PMBN-coated tube and the aldehyde tube, and the tubes were then allowed to stand at 80° C. for 1 hour. After washing with ultra pure water, the individual tubes were subjected to blocking.

The blocking herein means a process of inactivating, after immobilizing an oligo DNA to a carrier so as to give an immobilized primer, unreacted activated ester or aldehyde group portions which reside on the surface of the carrier, in order to prevent non-specific binding of DNA chain and RNA chain, and proteins and so forth of biological origin in the sample.

More specifically, as for the PMBN tube, each tube was dispensed with 400 µl of a 1 mol/l NaOH solution as a blocking solution, allowed to stand for 5 minutes at room temperature, removed with the blocking solution, and washed with ultra pure water.

As for the aldehyde tube, a blocking solution was prepared by dissolving 0.6 g sodium borohydride and 50 ml of ethanol into 180 ml of phosphate buffer, each tube was dispensed with 400 µl of the blocking solution, allowed to stand for 5 minutes at room temperature, removed with the blocking solution, and washed with ultra pure water.

After the blocking, 400 µl of a 1 wt % BSA-containing PBS(−) was spotted into each tube, allowed to stand at room temperature for 2 hours, and washed three times by dispensing and sucking to remove 400 µl of a washing solution containing 0.05 wt % Tween® 20 (Polyoxyethylene Sorbitan Monolaurate) in PBS(−), and the tubes were then dried.

TABLE 3

| SEQ ID NO: 4 |
|---|
| 5'-TTTTTTTTTTTTTTTTTTTTTTTTTTT-3' |

(Preparation of cDNA from Total RNA of HeLa Cell)

One hundred microliters of DEPC treated water, containing 1 µg of total RNA extracted from cultured HeLa cells was kept at 65° C. for 5 minutes, and then quenched on ice. The RNA solution was added with a reaction solution prepared by adding reverse transcriptase M-MLV (Rnase H−), 5× reverse transcriptase M-MLV buffer, RNase inhibitor (super), 20 mM of DATP, 20 mM of dGTP, 20 mM of dCTP, and DEPC treated water. Ten microliters each of this solution was dispensed into the individual tubes, and incubated at 42° C. for 1 hour. Some of the tubes after incubation were dispensed with 200 µl of a TE buffer (10 mM Tris/HCl (pH8.5), 1 mM EDTA), washed twice with the TE buffer, then washed with ultra pure water, and dried. Some of the tubes after incubation were added with RNase H, and incubated at 37° C. for 20 minutes. After the incubation, 200 µl of the TE buffer (10 mM Tris/HCl (pH8.5), 1 mM EDTA) was dispensed, and washed twice with the TE buffer, then with ultra pure water, and dried.

Twenty microliters each of a reaction solution, prepared by adding ExTaq™ HS, 10× ExTaq™ Buffer, 100 µM of Forward primer (SEQ ID NO:5), 100 µM of Reverse primer (SEQ ID NO:6), 20 mM of dTTP, 20 mM of dATP, 20 mM of dGTP, 20 mM of dCTP, and DEPC treated water, was dispensed into the individual tubes, and the PCR reaction was allowed to proceed therein. Forward primer and reverse primer were selected from human β-actin sequence. The sequence of the primer is shown in Table 4.

After the reaction, PCR products were confirmed by subjecting the PCR reaction solution in the individual tubes to electrophoresis.

TABLE 4

| Name of Primer | Sequence |
|---|---|
| Forward primer | SEQ ID NO: 5 |
| | 5'-ACTGGAACGGTGAAGGTGAC-3' |
| Reverse primer | SEQ ID NO: 6 |
| | 5'-CAGTGTACAGGTAAGCCCTG-3' |

The PCR products in the gel after the electrophoresis were dyed with ethidium bromide, and color density of the bands were converted into numerical expression using a fluorometric scanner. Values are shown in Table 5 below, assuming density of the band without RNase treatment in the aldehyde tube as 100. Amount of the products obtained by the PCR reaction may be known from comparison of these values. Larger values mean that larger amounts of product were obtained, and that the PCR reaction proceeded in an efficient manner. In this case, efficiency of the PCR reaction under the presence of RNA of the tube may be known, by comparison between the PMBN-coated tube and the aldehyde tube, and between presence and absence of the RNase treatment.

TABLE 5

Numerical Expression of Bands

| Tube | RNase treatment | |
|---|---|---|
| | presence | absence |
| PMBN-coated tube | 859 | 822 |

Example 3

RT-Q-PCR from Cell Lysate (Fabrication of PMBN-Coated Tube)

The individual tubes of a commercially-available PCR 8-tube-strip (made of polypropylene) was immersed in a 0.5 wt % solution of 2-methacryloyloxyethyl phosphorylcholine/butyl methacrylate/p-nitrophenyloxycarbonyl polyethylene glycol methacrylate copolymer (poly(MPC-co-BMA-co-NPMA) (PMBN), the individual groups are in a molar percentage of 25:74:1) in ethanol, so as to introduce a polymer substance having phosphorylcholine groups and activated ester groups to the surface of the tube, to thereby obtain a PMBN-coated tube. The tube will be referred to as "PMBN tube", hereinafter.

(Preparation of Aldehyde Tube)

A commercially-available PCR 8-tube-strip (made of polypropylene) was subjected to a treatment so as to raise hydrophilicity of the surface thereof, by low-temperature oxygen plasma treatment. Next, a treatment liquid for introducing amino group was prepared by dissolving γ-aminopropyl triethoxy silane, as an aminoalkyl silane, in methanol at a concentration of 5 wt %, the 8-tube-strip was immersed into the liquid for 2 hours, then taken out therefrom, immersed in ultra pure water, allowed to stand, and then the 8-tube-strip was taken out and dried. Glutaraldehyde solution was prepared by dissolving glutaraldehyde into PBS(−) at a concentration of 2 wt %, and the 8-tube-strip treated by alkylsilane was immersed in the glutaraldehyde solution, allowed to stand for 4 hours, the 8-tube-strip was then taken out, immersed into ultra pure water, washed and dried. By these processes, an aldehyde tube having aldehyde group on the surface thereof was obtained.

(Immobilization of Primer)

Immobilization of the primer onto the PMBN tube and the aldehyde tube were carried out by a method similar to that shown in Example 2.

(Purification of mRNA from HeLa Cells)

Cultured HeLa cells were washed several times, centrifuged to be obtained in a form of pellet in a tube, added with cell lysate containing guanidine, more thoroughly stirred by pipetting, and thereby the cell lysate were obtained as the target sample of the HeLa cells. Fifty microliters each of the solution, diluted step-wise, was dispensed into the PMBN-coated tube and the aldehyde tube, and the tubes were allowed to stand at room temperature for 15 minutes. After being allowed to stand, 200 μl each of a buffer solution containing a detergent was dispensed, and washed twice by repeating suction.

The mRNA having poly-A is captured by the dT primer on the surface of the tubes, so that any substances of biological origin other than the mRNA contained in the cell lysate may be removed.

(Synthesis of Solid-Phase cDNA from mRNA)

A reaction solution was prepared by adding reverse transcriptase M-MLV (Rnase H−), 5× reverse transcriptase M-MLV buffer, RNase inhibitor (Super), 20 mM of dTTP, 20 mM of dATP, 20 mM of dGTP, 20 mM of dCTP, and DEPC treated water. Fifty microliters of this liquid was dispensed into the individual tubes, and incubated at 42° C. for 15 minutes or longer. After incubation, the liquid was removed.

(PCR Reaction from Solid-Phase cDNA)

A reaction solution was prepared by adding TaKaRa ExTaq™ HS (from Takara Bio Inc.), 10× ExTaq™ buffer, 10 μM of PCR forward primer (SEQ ID NO:5), 10 μM of PCR reverse primer (SEQ ID NO:6), 20 mM of dTTP, 20 mM of dATP, 20 mM of dGTP, 20 mM of dCTP, and DEPC treated water, 50 μl each of this liquid was dispensed into the individual tubes, and quantitative PCR was carried out. The forward primer and the reverse primer herein were selected from human β-actin sequence. Sequences of the primer are shown in Table 4.

After the reaction, PCR products in the PCR reaction solution in the individual tubes were confirmed by electrophoresis.

(Quantitative PCR Reaction from Solid-Phase cDNA)

A reaction solution was prepared by adding TaKaRa Premix ExTaq™ Hot Start Version (from Takara Bio Inc.), 10 μM of PCR Forward primer (SEQ ID NO:5), 10 μM of PCR Reverse primer (SEQ ID NO:6), 20 mM of dTTP, 20 mM of dATP, 20 mM of dGTP, 20 mM of dCTP, and DEPC treated water, and 50 μl each of this liquid was dispensed into the individual tubes, and quantitative PCR was carried out. The forward primer and the reverse primer were selected from human β-actin sequence. Sequences of the primer are shown in Table 4.

(RT-PCR Reaction Using One-Step Reagent)

At present, one-step-type RT-PCR reaction solution, containing enzymes for reverse transcription reaction and enzymes for PCR reaction premixed therein, are commercially available from several reagent manufacturers. A step of synthesizing a solid-phase cDNA from mRNA, PCR reaction from the solid-phase cDNA, and a step of quantitative PCR may be carried out in a single reaction solution, by using this reagent.

A reaction solution was prepared by adding the one-step SYBR® PrimeScript® RT-PCR kit (from Takara Bio Inc.), 10 μM of PCR forward primer (SEQ ID NO:5), 10 μM of PCR reverse primer (SEQ ID NO:6), and DEPC treated water, and 50 μl each of this liquid was dispensed into the individual tubes, and quantitative PCR was carried out. The forward primer and the reverse primer herein were selected from human β-actin sequence. Sequences of the primer are shown in Table 4.

The PCR products were converted into numerical expression, using color density of bands obtained from electrophoresis. The values were shown in Table 6 below, assuming density of the band of the PCR product in the PMBN-coated tube as 100. Amount of the products obtained by the PCR reaction may be known from comparison of these values. Larger values mean that larger amounts of products were obtained, and that the PCR reaction proceeded in an efficient manner. Among the PCR reactions proceeded under the same conditions, any of those causing smaller variation in the values may be understood as being more stably carried out from the steps relevant to the cell lysate to the PCR products, proving better reproducibility.
(Table 6)

TABLE 6

| | Degree of Coloration (in numerical expression) | |
|---|---|---|
| | PMBN-coated tube | Aldehyde-coated tube |
| Test 1 | 7893 | 342 |
| Test 2 | 8230 | 617 |
| Test 3 | 8480 | 560 |

Figure 23:
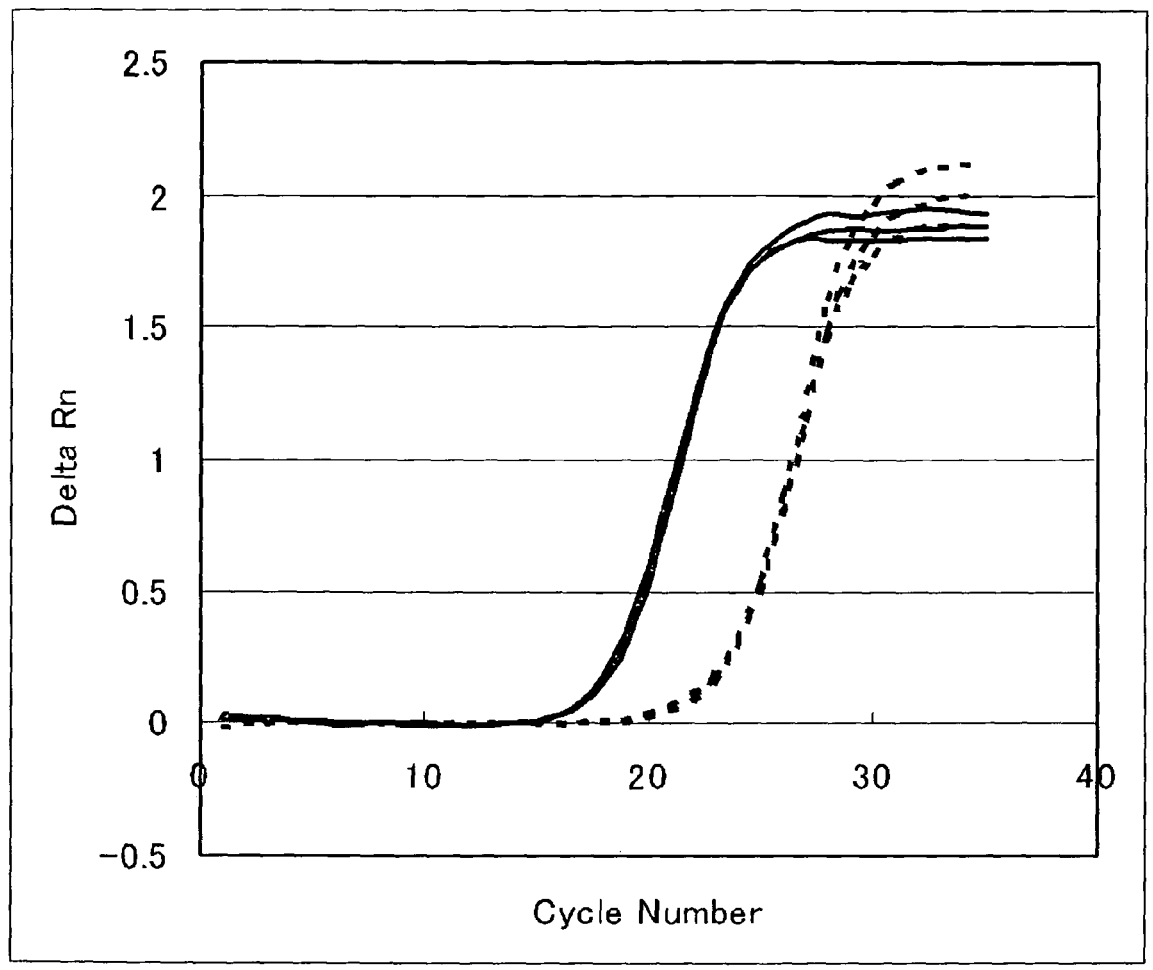
FIG. 23 A graph showing results of quantitative PCR according to an Example.

Amplification curves obtained by the quantitative PCR are shown in FIG. 23. Ct values obtained from the amplification curves are shown in Table 7. The Ct value are obtained as being dependent on the amount of template DNA at the beginning of the quantitative PCR reaction. More specifically, smaller Ct values mean larger amounts of DNA at the beginning, and smaller variation in the Ct values mean more stable proceeding of the steps relevant to the cell lysate to the PCR products, proving better reproducibility.
(Table 7)

TABLE 7

| | Ct Value | |
|---|---|---|
| | PMBN-coated tube | Aldehyde-coated tube |
| Test 1 | 18.22 | 23.53 |
| Test 2 | 18.28 | 23.30 |
| Test 3 | 18.53 | 23.28 |

Example 4

Preparation of cDNA Using Random Primer (Purification of mRNA from HeLa Cells)
Cultured HeLa cells were washed several times, centrifuged to be obtained in a form of pellet in the tube, added with cell lysate containing guanidine, more thoroughly stirred by pipetting, and thereby the cell lysate was obtained as the target sample of the HeLa cells. Fifty microliters each of the solution, diluted step-wise, was dispensed into the PMBN-coated tube and the aldehyde tube, and the tubes were allowed to stand still at room temperature for 15 minutes After being allowed to stand still, 200 µl each of a buffer solution containing a detergent was dispensed, and washed twice by repeating suction.

(Synthesis of Liquid-Phase cDNA from mRNA)
A reaction solution was prepared by adding reverse transcriptase M-MLV (Rnase H−), 5× reverse transcriptase M-MLV buffer, 10 µl of random primer, RNase Inhibitor (Super), 20 mM of dTTP, 20 mM of dATP, 20 mM of dGTP, 20 mM of dCTP, and DEPC treated water. Fifty microliters of this liquid was dispensed into the individual tubes, and incubated at 42° C. for 15 minutes or longer.

The Liquid was diluted step-wisely, and dispensed into the PCR tubes together with a liquid prepared by adding SYBR® Premix ExTaq™ (from Takara Bio Inc.), 10 µM of PCR forward primer (SEQ ID NO:5), 10 µM of PCR Reverse primer (SEQ ID NO:6), 20 mM of dTTP, 20 mM of dATP, 20 mM of dGTP, 20 mM of dCTP, and DEPC treated water, and quantitative PCR was carried out. The forward primer and the reverse primer herein were selected from human β-actin sequence. Sequences of the primer are shown in Table 4.

Figure 24:
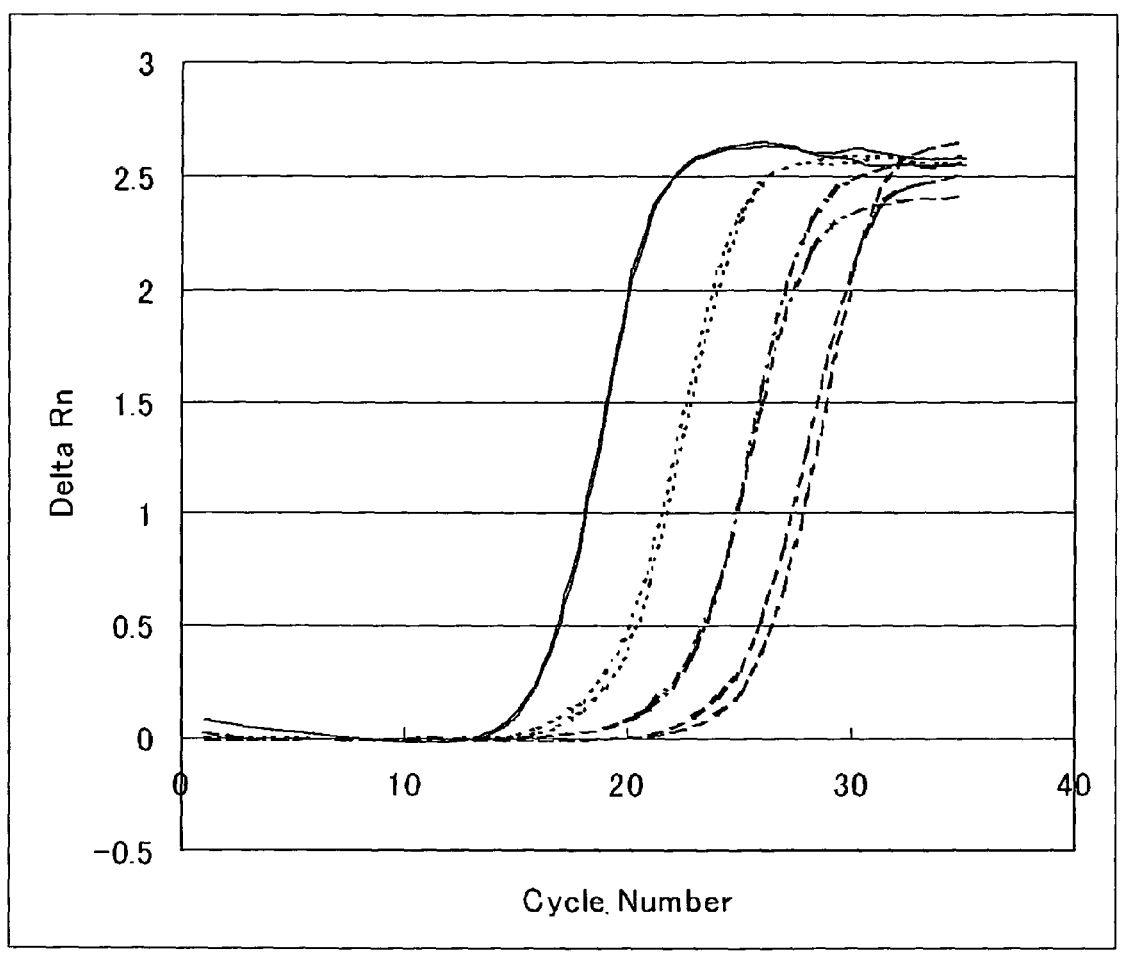
FIG. 24 A graph showing results of quantitative PCR according to an Example.

Amplification curves obtained by the quantitative PCR are shown in FIG. 24. Ct values obtained from the amplification curves are shown in Table 8. The Ct value are obtained as being dependent on the amount of template DNA at the beginning of the quantitative PCR reaction. More specifically, smaller Ct values mean larger amounts of DNA at the beginning, and smaller variation in the Ct values mean more stable proceeding of the steps relevant to the cell lysate to the PCR products, proving better reproducibility.
(Table 8)

TABLE 8

| | Ct Value PMBN-coated tube | |
|---|---|---|
| ×1 Dilution | 16.57 | 16.72 |
| ×¼ Dilution | 19.69 | 20.12 |
| ×⅛ Dilution | 22.96 | 23.15 |
| ×1/16 Dilution | 25.62 | 26.22 |

Specific embodiments of the present invention will be shown below.
(A-1)
An RNA Detection Method Detecting a Target RNA Chain from a reaction system containing cell lysate of target cells, using a substrate having on the surface thereof a polymer substance which contains a first unit having a group derived from a phosphate ester composing the hydrophilic portion of a phospholipid and a second unit having a carboxylic acid derivative group composed of an electron-attractive substitutional group bound to a carbonyl group, while being provided with at least one reaction space, the reaction space having an immobilized nucleic acid primer immobilized therein;
(A-2)
The RNA detection method described in (A-1), which includes:
a first step introducing, into the reaction space provided on the substrate, a sample containing the cell lysate, an enzyme system for DNA chain extension and nucleotide monomers, and allowing a DNA chain extension reaction to proceed ahead of the immobilized DNA primer, while using an RNA chain contained in the cell lysate as a template; and
a second step detecting a DNA chain obtained by the extension reaction;
(A-3)
The RNA detection method described in (A-2),
wherein the enzyme system for DNA chain extension used in the first step is either a reverse transcriptase, or a combination of a DNA ligase and a reverse transcriptase;
(A-4)
The RNA detection method described in (A-2),
wherein at least one species of the nucleotide monomers, contained in the sample introduced in the first step, is labeled;
(A-5)
The RNA detection method described in (A-1), which includes:
a first step introducing, into the reaction space provided on the substrate, a sample containing the cell lysate, an enzyme system for DNA chain extension and nucleotide monomers, and allowing a DNA chain extension reaction to proceed ahead of the immobilized DNA primer, while using an RNA chain contained in the cell lysate as a template, to thereby form a cDNA chain;
a second step decomposing the RNA chain in the reaction system, after the DNA chain extension reaction;

a third step introducing, into the reaction system containing the cDNA chain, a mixture containing a DNA primer for extension, an enzyme system for DNA chain extension and nucleotide monomers, and synthesizing a double-strand DNA, while using the cDNA chain as a template; and a fourth step detecting the synthesized double-strand DNA;

(A-6)

The RNA detection method described in (A-5), wherein at least one species of the nucleotide monomers, contained in the sample introduced in the third step, is labeled;

(A-7)

The RNA detection method described in (A-1), which includes:

a first step introducing, into the reaction space provided on the substrate, a sample containing the cell lysate, an enzyme system for DNA chain extension and nucleotide monomers, and allowing a DNA chain extension reaction to proceed ahead of the immobilized DNA primer, while using an RNA chain contained in the cell lysate as a template, to thereby form a cDNA chain;

a second step decomposing the RNA chain in the reaction system, after the DNA chain extension reaction;

a third step introducing, into the reaction system containing the cDNA chain, a mixture containing a DNA primer for extension, an enzyme system for DNA chain extension and nucleotide monomers, and synthesizing a double-strand DNA, while using the cDNA chain as a template;

a fourth step synthesizing double-strand DNAs, while respectively using the individual single-strand DNAs obtained by heat denaturation of the double-strand DNA as templates, to thereby amplify the double-strand DNA; and a fifth step detecting the amplified double-strand DNAs;

(A-8)

The RNA detection method described in any one of (A-5) to (A-7), wherein the enzyme system for DNA chain extension used in the first step is either a reverse transcriptase, or a combination of a DNA ligase and a reverse transcriptase;

(A-9)

The RNA detection method described in any one of (A-5) to (A-7), wherein, in the third step, the extension reaction of DNA chain ahead of the DNA primer for extension is proceeded by allowing the whole process to take place in a single liquid phase system, the whole process includes:

raising the reaction system up to a temperature at which the DNA chain causes heat denaturation (referred to as "heat denaturation temperature", hereinafter); and lowering temperature of the reaction system down to a temperature for annealing (referred to as "annealing temperature", hereinafter), (A-10)

The RNA detection method described in (A-1), wherein the group derived from a phosphate ester contained in the first unit of the polymer substance is any one of phosphorylcholine group, phosphorylethanolamine group, phosphorylserine group, phosphorylinositol group, phosphorylglycerol group, and phosphatidyl phosphorylglycerol group;

(A-11)

The RNA detection method described in (A-1), wherein the immobilized DNA primer is immobilized to the surface of the substrate, by forming a covalent bond at the portion of the carboxylic acid derivative group located on the surface of the reaction space of the substrate;

(A-12)

The RNA detection method described in (A-1), wherein the polymer substance has a third unit containing a butyl methacrylate group;

(A-13)

The RNA detection method described in (A-1) or (A-12), wherein the substrate contains, in addition to the polymer substance, a second polymer substance having a first unit containing a group derived from a phosphate ester composing the hydrophilic portion of a phospholipid, and a third unit containing a butyl methacrylate group;

(A-14)

The RNA detection method described in (A-1), wherein the substrate is composed of a plastic material;

(A-15)

The RNA detection method described in (A-1), wherein the substrate configures a plurality of arrays having reaction spaces independent from each other, each array having an immobilized DNA primer respectively immobilized therein;

(B-1)

An RNA detection method detecting a target RNA chain from a reaction system containing cell lysate of target cells, using a carrier having on the surface thereof a polymer substance which contains a first unit having a group derived from a phosphate ester composing the hydrophilic portion of a phospholipid and a second unit having a carboxylic acid derivative group composed of an electron-attractive substitutional group bound to a carbonyl group, while being provided with at least one reaction space, the method includes:

a first step preparing a primer-immobilized carrier by immobilizing a primer for DNA extension onto the surface of the carrier;

a second step introducing, into the reaction space provided on the carrier, a sample containing the cell lysate, an enzyme system for DNA chain extension and nucleotide monomers, and allowing a DNA chain extension reaction to proceed ahead of the immobilized DNA primer, while using an RNA chain contained in the cell lysate as a template, to thereby form a cDNA chain;

a third step introducing, into the reaction system containing the cDNA chain, a mixture containing a DNA primer for extension, an enzyme system for DNA chain extension and nucleotide monomers, and synthesizing a double-strand DNA, while using the cDNA chain as a template; and a fourth step detecting the synthesized double-strand DNA, without decomposing the RNA chain between the second step and the third step;

(B-2)

The RNA detection method described in (B-1), wherein at least one species of the nucleotide monomers, contained in the sample introduced in the third step, is labeled;

(B-3)

An RNA detection method detecting a target RNA chain from a reaction system containing cell lysate of target cells, using a carrier having on the surface thereof a polymer substance which contains a first unit having a group derived from a phosphate ester composing the hydrophilic portion of a phospholipid and a second unit having a carboxylic acid derivative group composed of an electron-attractive substitutional group bound to a carbonyl group, while being provided with at least one reaction space, the method includes:

a first step preparing a primer-immobilized carrier by immobilizing a primer for DNA extension onto the surface of the carrier;

a second step introducing, into the reaction space provided on the carrier, a sample containing the cell lysate, an enzyme system for DNA chain extension and nucleotide monomers, and allowing a DNA chain extension reaction to proceed ahead of the immobilized DNA primer, while using an RNA chain contained in the cell lysate as a template, to thereby form a cDNA chain;

a third step introducing, into the reaction system containing the cDNA chain, a mixture containing a DNA primer for extension, an enzyme system for DNA chain extension and nucleotide monomers, and synthesizing a double-strand DNA, while using the cDNA chain as a template;

a fourth step synthesizing double-strand DNAs, while respectively using the individual single-strand DNAs obtained by heat denaturation of the double-strand DNA as templates, to thereby amplify the double-strand DNA; and a fifth step detecting the amplified double-strand DNAS, without decomposing the RNA chain between the second step and the third step;

(B-4)
The RNA Detection method described in any one of (B-1) to (B-3),
wherein the enzyme system for DNA chain extension used in the first step is either a reverse transcriptase, or a combination of a DNA ligase and a reverse transcriptase;

(B-5)
The RNA detection method described in any one of (B-1) to (B-3),
wherein, in the fourth step, the extension reaction of DNA chain ahead of the DNA primer for extension is proceeded by allowing the whole process to take place in a single liquid phase system, the whole process includes:
raising the reaction system up to a temperature at which the DNA chain causes heat denaturation (referred to as "heat denaturation temperature", hereinafter); and
lowering temperature of the reaction system down to a temperature for annealing (referred to as "annealing temperature", hereinafter), (B-6)
The RNA detection method described in (B-1) or (B-3),
wherein the group derived from a phosphate ester contained in the first unit of the polymer substance is any one of phosphorylcholine group, phosphorylethanolamine group, phosphorylserine group, phosphorylinositol group, phosphorylglycerol group, and phosphatidyl phosphorylglycerol group;

(B-7)
The RNA detection method described in (B-1) or (B-3),
wherein the primer for DNA extension is immobilized to the surface of the carrier, by forming a covalent bond at the portion of the carboxylic acid derivative group located on the surface of the reaction space of the carrier;

(B-8)
The RNA detection method described in (B-1) or (B-3),
wherein the polymer substance has a third unit containing a butyl methacrylate group;

(B-9)
The RNA detection method described in (B-1) or (B-3),
wherein the carrier contains, in addition to the polymer substance, a second polymer substance having a first unit containing a group derived from a phosphate (ester composing the hydrophilic portion of a phospholipid, and a third unit containing a butyl methacrylate group;

(B-10)
The RNA detection method described in (B-1) or (B-3),
wherein the reaction space has a form of tube or well;

(B-11)
The RNA detection method described in (B-1) or (B-3),
wherein the carrier is composed of a plastic material;

(B-12)
The RNA detection method described in (B-1) or (B-3),
wherein the carrier configures a plurality of arrays having reaction spaces independent from each other, each array having a primer for DNA extension respectively immobilized therein.

[Table of Sequence]

---

The invention claimed is:

1. An RNA detection method detecting, from a reaction system containing a target sample, a target RNA chain originated from said target sample, which comprises
providing a reaction space on a substrate surface, said substrate surface is composed of a plastic material and has a polymer substance which contains (a) a first unit having a group derived from a phosphate ester composing the hydrophilic portion of a phospholipid and a second unit having a carboxylic acid derivative group composed of an electron-attractive substitutional group bound to a carbonyl group, and (b) an immobilized DNA primer,
allowing a DNA chain extension reaction to proceed ahead of said immobilized DNA primer in the reaction space, while using said target RNA chain in said target sample as a template, and
detecting a DNA product.

2. The RNA detection method as claimed in claim 1, comprising:
a first step introducing, into said reaction space, said target sample, an enzyme system for DNA chain extension and nucleotide monomers, and then allowing said DNA chain extension reaction to proceed ahead of said immobilized DNA primer, and
wherein the detecting a DNA product is a second step comprising detecting a DNA chain obtained by said extension reaction.

3. The RNA detection method as claimed in claim 2, wherein said enzyme system for DNA chain extension used in said first step is either a reverse transcriptase, or a combination of a DNA ligase and a reverse transcriptase.

4. The RNA detection method as claimed in claim 2, wherein at least one species of said nucleotide monomers, contained in said sample introduced in said first step, is labeled.

5. The RNA detection method as claimed in claim 1, comprising:
a first step introducing, into said reaction space, said target sample, an enzyme system for DNA chain extension and nucleotide monomers, and then allowing said DNA chain extension reaction to proceed ahead of said immobilized DNA primer, to thereby synthesize a cDNA chain;
a second step decomposing said target RNA chain in said reaction system, after said DNA chain extension reaction;
a third step introducing, into said reaction system containing said cDNA chain, a mixture containing a DNA primer for extension, an enzyme system for DNA chain extension and nucleotide monomers, and synthesizing a double-strand DNA, while using said cDNA chain as a template; and
wherein the detecting a DNA product is a fourth step comprising detecting said synthesized double-strand DNA.

6. The RNA detection method as claimed in claim 5, wherein at least one species of said nucleotide monomers, contained in said mixture introduced in said third step, is labeled.

7. The RNA detection method as claimed in claim 1, comprising:
a first step introducing, into said reaction space, said target sample, an enzyme system for DNA chain extension and nucleotide monomers, and then allowing said DNA chain extension reaction to proceed ahead of said immobilized DNA primer, to thereby synthesize a cDNA chain;

a second step decomposing said target RNA chain in said reaction system, after said DNA chain extension reaction;

a third step introducing, into said reaction system containing said cDNA chain, a mixture containing a DNA primer for extension, an enzyme system for DNA chain extension and nucleotide monomers, and synthesizing a double-strand DNA, while using said cDNA chain as a template;

a fourth step synthesizing double-strand DNAs, while respectively using individual single-strand DNAs obtained by heat denaturation of said double-strand DNA as templates, to thereby amplify the said double-strand DNA; and wherein the detecting a DNA product is a fifth step comprising detecting said amplified double-strand DNAs.

8. The RNA detection method as claimed in claim 5,
wherein said enzyme system for DNA chain extension used in said first step is either a reverse transcriptase, or a combination of a DNA ligase and a reverse transcriptase.

9. The RNA detection method as claimed in claim 5,
wherein, in said third step, said DNA chain extension reaction ahead of said DNA primer for extension is proceeded by allowing the whole process to take place in a single liquid phase system, said whole process includes:
raising said reaction system up to a temperature for denaturation; and
lowering temperature of said reaction system down to a temperature for annealing.

10. The RNA detection method as claimed in claim 1, comprising:
a first step introducing, into said reaction space, said target sample, an enzyme system for DNA chain extension and nucleotide monomers, and then allowing said DNA chain extension reaction to proceed ahead of said immobilized DNA primer, to thereby synthesize a cDNA chain;
a second step introducing, into the reaction system containing said cDNA chain, a mixture containing a DNA primer for extension, an enzyme system for DNA chain extension and nucleotide monomers, and synthesizing a double-strand DNA, while using said cDNA chain as a template; and
wherein the detecting a DNA product is a third step comprising detecting said synthesized double-strand DNA, without decomposing the RNA chain between said first step and said second step.

11. The RNA detection method as claimed in claim 10,
wherein at least one species of said nucleotide monomers, contained in said mixture introduced in said second step, is labeled.

12. The RNA detection method as claimed in claim 1, comprising:
a first step introducing, into said reaction space, said target sample, an enzyme system for DNA chain extension and nucleotide monomers, and then allowing said DNA chain extension reaction to proceed ahead of said immobilized DNA primer, to thereby form a cDNA chain;
a second step introducing, into the reaction system containing said cDNA chain, a mixture containing a DNA primer for extension, an enzyme system for DNA chain extension and nucleotide monomers, and synthesizing a double-strand DNA, while using said cDNA chain as a template;
a third step synthesizing double-strand DNAs, while respectively using individual single-strand DNAs obtained by heat denaturation of said double-strand DNA as templates, to thereby amplify the said double-strand DNA; and
wherein the detecting a DNA product is a fourth step comprising detecting said amplified double-strand DNAs, without decomposing the RNA chain between said first step and said second step.

13. The RNA detection method as claimed in claim 10,
wherein said enzyme system for DNA chain extension used in said first step is either a reverse transcriptase, or a combination of a DNA ligase and a reverse transcriptase.

14. The RNA detection method as claimed in claim 10,
wherein, in said second step, said DNA chain extension reaction ahead of said DNA primer for extension is proceeded by allowing the whole process to take place in a single liquid phase system, said whole process includes:
raising said reaction system up to a temperature for denaturation; and
lowering temperature of said reaction system down to a temperature for annealing.

15. The RNA detection method as claimed in claim 1, characterized as a reverse transcription-polymerase chain reaction method, comprising:
transferring said target sample into said reaction space having the substrate surface described in claim 1;
hybridizing an mRNA in said target sample with said immobilized DNA primer;
allowing RT-PCR to proceed in said reaction space using a buffer solution; and wherein the detecting a DNA product comprises
detecting a desired PCR product.

16. The RNA detection method as claimed in claim 15,
wherein, at detection, said desired PCR product is quantified by measuring fluorescence, or allowing fluorescence or chemical luminescence to emit, with nucleic acid dyeing.

17. The RNA detection method as claimed in claim 15,
wherein said allowing RT-PCR to proceed is a liquid phase RT-PCR, proceeded without exchanging a buffer solution in said reaction space, or without removing said mRNA hybridized with said immobilized DNA primer, using a reaction solution containing a reverse transcriptase and a DNA polymerase, or a reaction solution containing rTth polymerase.

18. The RNA detection method as claimed in claim 15,
wherein said allowing RT-PCR to proceed is an RT-PCR which includes:
allowing hybridization of said mRNA with said immobilized DNA primer to proceed;
introducing, into said reaction system containing said mRNA, a DNA primer for extension and nucleotide monomers;
allowing a reverse transcription reaction and said DNA chain extension reaction to proceed ahead of said immobilized DNA primer, while using said target RNA chain contained in said target sample as the template, to thereby synthesize a cDNA chain on said substrate surface; and
allowing PCR to proceed using a DNA polymerase.

19. The RNA detection method as claimed in claim 18, further comprising:
  washing, after detecting said desired PCR product, so as to leave said cDNA chain on said substrate surface, allowing PCR to proceed using a primer same as, or different from that used at allowing RT-PCR to proceed, and wherein the detecting a DNA product comprises measuring the desired PCR product.

20. The RNA detection method as claimed in claim 19, repeating said washing, said allowing PCR to proceed, and said measuring.

21. The RNA detection method as claimed in claim 18, wherein at least one species of said nucleotide monomers, contained in said sample introduced in said allowing RT-PCR to proceed, is labeled.

22. The RNA detection method as claimed in claim 1, comprising:
  transferring said target sample into said reaction space having said substrate surface described in claim 1;
  hybridizing an mRNA in said target sample with said immobilized DNA primer;
  introducing a reaction solution for reverse transcription, containing a primer for DNA chain extension, into a liquid phase; and
  producing a liquid-phase cDNA by reverse transcription.

23. The RNA detection method as claimed in claim 22, further comprising:
  amplifying DNA or RNA using said liquid-phase cDNA.

24. The RNA detection method as claimed in claim 22, wherein at least one species of nucleotide monomers, which is contained in said reaction solution for reverse transcription, is labeled.

25. The RNA detection method as claimed in claim 1, wherein said reaction space is a PCR tube or a PCR microplate.

26. The RNA detection method as claimed in claim 1, wherein said immobilized DNA primer is an oligo dT.

27. The RNA detection method as claimed in claim 1, wherein said target sample contains guanidine or protease or phenol.

28. The RNA detection method as claimed in claim 1, wherein said target sample contains a reagent for inhibiting RNase activity, or inactivating RNase, and is prepared using a buffer solution for adjusting pH and salt concentration for hybridization.

29. The RNA detection method as claimed in claim 1, wherein the group derived from a phosphate ester contained in the first unit of said polymer substance is any one of phosphorylcholine group, phosphorylethanolamine group, phosphorylserine group, phosphorylinositol group, phosphorylglycerol group, and phosphatidyl phosphorylglycerol group.

30. The RNA detection method as claimed in claim 1, wherein said immobilized DNA primer is immobilized to said substrate surface, by forming a covalent bond at a portion of said carboxylic acid derivative group.

31. The RNA detection method as claimed in claim 1, wherein said polymer substance has a third unit containing a butyl methacrylate group.

32. The RNA detection method as claimed in claim 1, wherein said substrate surface contains, in addition to said polymer substance, a second polymer substance having a first unit containing a group derived from a phosphate ester composing the hydrophilic portion of a phospholipid, and a third unit containing a butyl methacrylate group.

33. The RNA detection method as claimed in claim 1, wherein said reaction space has a form of tube or well.

34. The RNA detection method as claimed in claim 1, wherein the substrate surface is provided on a carrier having a plurality of arrays having additional reaction spaces independent from each other, each array having a nucleic acid primer respectively immobilized therein.

* * * * *